United States Patent
Rosocha et al.

(10) Patent No.: US 9,902,699 B2
(45) Date of Patent: Feb. 27, 2018

(54) SYNTHESIS OF TETRAHYDROISOQUINOLINES FROM 2-METHYL-1-PHENYL SUBSTITUTED INDENES

(71) Applicant: Gregory Rosocha, Toronto (CA)

(72) Inventors: Gregory Rosocha, Toronto (CA); Robert Batey, Toronto (CA)

(73) Assignee: Gregory Rosocha, Toronto (CA)

( * ) Notice: Subject to any disclaimer, the term of this patent is extended or adjusted under 35 U.S.C. 154(b) by 0 days.

(21) Appl. No.: 14/437,655

(22) PCT Filed: Oct. 24, 2012

(86) PCT No.: PCT/IB2012/002070
§ 371 (c)(1),
(2) Date: Apr. 22, 2015

(87) PCT Pub. No.: WO2014/064476
PCT Pub. Date: May 1, 2014

(65) Prior Publication Data
US 2015/0284332 A1    Oct. 8, 2015

(51) Int. Cl.
*C07D 217/02* (2006.01)
*C07D 217/04* (2006.01)

(52) U.S. Cl.
CPC ......... *C07D 217/02* (2013.01); *C07D 217/04* (2013.01)

(58) Field of Classification Search
None
See application file for complete search history.

(56) References Cited

PUBLICATIONS

Dime et al. "Synthesis of Isoquinolines from Indenes" The Journal of Organic Chemistry, 1981, vol. 46, issue 24, pp. 4999-5000.*
Gregory S.Rosocha, "Development and Investigation of Electrocyclization Reactions Leading Towards Indene and Thiatriazole Formation and Their Functionalization", A thesis submitted in conformity with the requirements for the degree of Derctor of Philosophy, Department of Chemistry, University of Toronto. Toronto, Ontario, Canada, 2011.*
International Preliminary Report for PCT/IB2012/002070 dated Jan. 14, 2015, pp. 1-6.*
CIPO Examination Report dated Nov. 1, 2017.

* cited by examiner

*Primary Examiner* — Zinna Northington Davis
(74) *Attorney, Agent, or Firm* — Chumak & Company LLP

(57) ABSTRACT

A procedure for the synthesis of tetrahydroisoquinolines from 2-methyl-1-phenyl substituted indene is described. The process involves the use of osmium tetroxide to cleave the indene double bond forming the keto aldehyde product, which is then combined with a substituted amine forming the substituted isoquinoline. Isoquinolines can be useful as industrial products in the chemical, agrochemical, oil and gas industry, as well as useful as medicaments in the pharmaceutical industry.

24 Claims, 21 Drawing Sheets

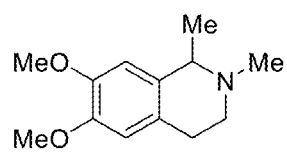
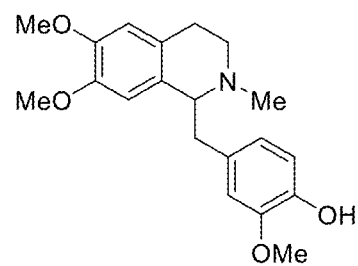
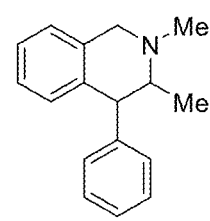
± Carnegine      ± Laudanine      1,2,3,4-tetrahydroisoquinoline
4      5      6
FIG. 2

| 1,2,3,4-tetrahydroisoquinoline | Name<br>Chemical Formula<br>Molecular Weight (g/mol) | Yield<br>d.e. |
|---|---|---|
| 7 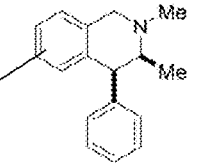 | (3S,4S)-2,3-dimethyl-4-phenyl-1,2,3,4-tetrahydroisoquinoline<br><br>$C_{17}H_{19}N$<br>237.35 | 92%<br>98:2 |
| 8 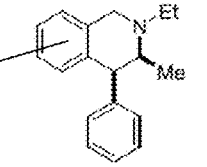 | (3S,4S)-2-ethyl-3-methyl-4-phenyl-1,2,3,4-tetrahydroisoquinoline<br><br>$C_{18}H_{21}N$<br>251.37 | 62%<br>95:5 |
| 9 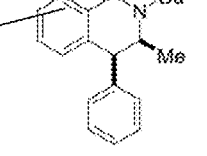 | (3S,4S)-2-butyl-3-methyl-4-phenyl-1,2,3,4-tetrahydroisoquinoline<br><br>$C_{20}H_{25}N$<br>279.43 | 85%<br>98:2 |
| 10 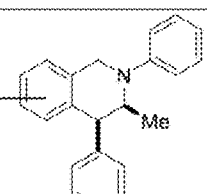 | (3S,4S)-3-methyl-2,4-diphenyl-1,2,3,4-tetrahydroisoquinoline<br><br>$C_{22}H_{21}N$<br>299.42 | 73-99%<br>98:2 |
| 11 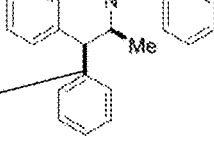 | (3S,4S)-2-benzyl-3-methyl-4-phenyl-1,2,3,4-tetrahydroisoquinoline<br><br>$C_{23}H_{23}N$<br>313.44 | 72%<br>95:5 |

FIG. 3

| 1,2,3,4-tetrahydroisoquinoline | Name<br>Chemical Formula<br>Molecular Weight (g/mol) | Yield<br>d.e. |
|---|---|---|
| 12  | (3S,4S)-3-methyl-2-phenethyl-4-phenyl-1,2,3,4-tetrahydroisoquinoline<br><br>C$_{24}$H$_{25}$N<br>327.47 | 47-99%<br>95:5 |
| 13 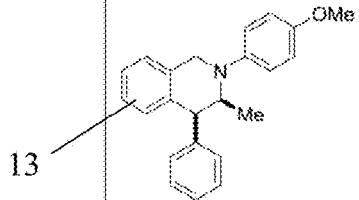 | (3S,4S)-2-(4-methoxyphenyl)-3-methyl-4-phenyl-1,2,3,4-tetrahydroisoquinoline<br><br>C$_{23}$H$_{23}$NO<br>329.44 | 75%<br>98:2 |
| 14 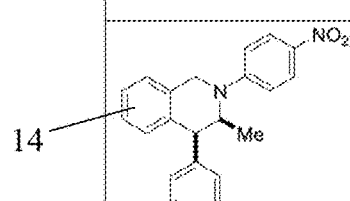 | (3S,4S)-3-methyl-2-(4-nitrophenyl)-4-phenyl-1,2,3,4-tetrahydroisoquinoline<br><br>C$_{22}$H$_{20}$N$_2$O$_2$<br>344.41 | 28%<br>70:30 |
| 15 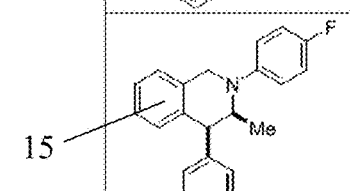 | (3S,4S)-2-(4-fluorophenyl)-3-methyl-4-phenyl-1,2,3,4-tetrahydroisoquinoline<br><br>C$_{22}$H$_{20}$FN<br>317.41 | 72%<br>90:10 |
| 16 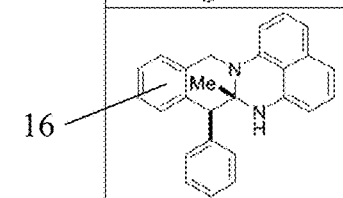 | (7aS,8S)-7a-methyl-8-phenyl-7,7a,8,13-tetrahydroisoquinolino[2,3-a]perimidine<br><br>C$_{26}$H$_{22}$N$_2$<br>362.48 | 49%<br>98:2 |

SYNTHESIS OF TETRAHYDROISOQUINOLINES FROM 2-METHYL-1-PHENYL SUBSTITUTED INDENES

FIELD OF THE INVENTION

The field of the invention is a new process to make 1,2,3,4-tetrahydroisoquinoline chemicals and medicaments using a new method that is very efficient, produces less waste and provides high diastereoselectivity. An efficient process to make 1,2,3,4-tetrahydroisoquinolines and a micro flow reactor is disclosed that can be used to make substituted 1,2,3,4-tetrahydroisoquinolines that can be used as industrial chemicals or medicaments.

BACKGROUND OF THE INVENTION 1,2,3,4-tetrahydroisoquinolines are chemicals that provide a high level of chemical variability. This chemical property provides an opportunity to make different chemicals that are engineered with desired properties that are used by different industries. 1,2,3,4-tetrahydroisoquinolines are important chemicals that have been used by the pharmaceutical and chemical industry for many years. They have many properties that make them desirable targets of development by the pharmaceutical industry because of their medicinal uses and they continue to be manufactured by the chemical industry on larger scales. They have been used for the treatment of neurological diseases such as depression, schizophrenia and Parkinson's, and are used as neuromuscular anesthetics, antivirals, antimicrobials, antiparasitics and disinfectants. For example, the methyl containing 1,2,3,4-tetrahydroisoquinolines have been investigated for the treatment of Parkinson's disease. In addition, they have been researched for use as calcium agonists to treat other diseases. The high bioavailability, metabolic clearance, and general safety of use of 1,2,3,4-tetrahydroisoquinolines makes them very good medicaments that can be used for the treatment of many diseases. The large chemical variability that exists with 1,2,3,4-tetrahydroisoquinolines allows this class of chemicals to have different medicinal properties.

In addition to the medicinal properties of 1,2,3,4-tetrahydroisoquinolines, several other industries use these chemicals as industrial surfactants, disinfectants, detergents and corrosion inhibitors. These chemicals are also used as additives for oil and gas applications because of the different chemical properties that 1,2,3,4-tetrahydroisoquinolines provide. In addition, these chemicals have been used as pesticides, herbicides and wood preservatives because of the rapid acting and the biodegradable properties that these chemicals have. These desirable chemical properties provide added benefits because the chemicals are not long lasting providing lower environmental impact than other industrial chemicals or additives. Further, 1,2,3,4-tetrahydroisoquinolines are safer to use and handle by personnel providing advantages in safety.

The synthesis of 1,2,3,4-tetrahydroisoquinolines can be accomplished using batch or micro flow scales. Typical batch and flow methods include using the Pictet-Spangler reaction to make isoquinolines from aromatics. However, chemical yields generally tend to be lower without the aid of a flow reactor due to lower process efficiency and increased waste production. Another method includes the Bischler-Napierski reaction which often uses phosphorous containing chemicals that are dangerous and are difficult to use because of safety concerns and are problematic to store for prolonged periods of time. In addition, such methods have multiple steps and do not provide high diastereoselectivities in the final products that are formed. In addition, the starting materials are very expensive and can be difficult to obtain worldwide. These disadvantages can lead to chemical processes that are not efficient and can be very expensive. Therefore, it is beneficial and advantageous to have a process that can make 1,2,3,4-tetrahydroisoquinolines having a high diastereoselectivity and chemical variability in an efficient way. Such a process would provide new 1,2,3,4-tetrahydroisoquinolines with different properties that can be used by many industries.

The 1,2,3,4-tetrahydroisoquinolines that are made using the process of the present invention are made using substituted methyl and phenyl indene chemicals. These indene chemicals are petroleum derived chemicals that are found in crude oil, heavy oil and in other biomass. In addition, they are naturally occurring C9 chemicals that are found in varying quantities in bitumen and coal. Indenes are available in large quantities and can be purchased from chemical corporations worldwide in multi ton amounts. Several indene blends are commercially available that contain different isomers of indene including the methyl and phenyl substituted indenes. This availability from natural sources provides a very inexpensive chemical that is used for the process of the present invention. For example, they can be combined with additives to make a blended high energy fuel that is used by the marine industry. In addition, indenes are used as a chemical component by the plastics industry to make different polymeric products. The indene starting materials that are used in the process of the present invention are very inexpensive providing an economically feasible chemical to be used to make other high value chemicals like 1,2,3,4-tetrahydroisoquinoline that have uses for many industries. The process of the present invention overcomes many problems with current processes that have low chemical yields of final products, unwanted waste products, starting chemical availability, process operational costs, additional safety requirements, and reduced economic feasibility.

In addition, the process of the present invention uses a metal salt blend containing osmium to make 1,2,3,4-tetrahydroisoquinolines. The use of osmium has many advantages because different chemical and pharmaceutical products can be made with high chemical selectivity. Osmium has been used to make diols, carbonyl products and other high value products that are important chemicals used by the chemical and pharmaceutical industry. This solid metal chemical is easily available for large scale applications and in smaller scale applications. Further, osmium can be used as a catalyst to provide lower chemical process costs. These advantages allow osmium to be a versatile and beneficial chemical to use for a chemical process.

Further, the process of the present invention involves the use of a micro flow reactor to make 1,2,3,4-tetrahydroisoquinolines. Flow reactors have been used to make chemicals but have not been disclosed in the art to make highly substituted 1,2,3,4-tetrahydroisoquinolines from indenes leading to more structurally complex molecules. Flow reactors and microreactors can be purchased from different suppliers and provide many advantages in chemical synthesis. Safety concerns are minimized because smaller amounts of chemicals are used, more precise control of temperature and chemical concentrations is achieved and finer control of reaction rates is obtained. The smaller quantities of chemicals that are used minimize explosion and other hazards involved with large scale batch chemistry. Further, the modular design minimizes human exposure to toxic chemicals when making chemical products. In addition, the very precise control of chemical selectivity, concentration, and temperature become very easy to control providing a way to optimize and manufacture chemicals in a shorter period of time providing economic benefits. Further, micro reactors and flow reactors can be numbered up to provide multi ton chemical production. Multi ton quantities of high value chemicals have been made using micro reactors and flow reactors.

Finally, the high level of control that micro reactors and flow reactors can achieve, provide advantages in chemical synthesis when expensive chemicals are used. Currently, micro flow reactors that use osmium to make 1,2,3,4-tetrahydroisoquinolines do not exist. Osmium is expensive and the ability to efficiently use osmium while minimizing waste can provide many advantages from lower operational costs and safety. The development of a micro flow reactor that uses osmium to make 1,2,3,4-tetrahydroisoquinolines can be beneficial for several industries including the chemical, pharmaceutical, and petroleum industries because of the increase in efficiencies. The process of the present invention provides a more efficient method to make 1,2,3,4-tetrhaydroisoquinolines that can use a micro flow device.

DETAILED SUMMARY OF INVENTION

The present invention is a two-step process that uses an osmium salt blend and a solvent blend for the oxidative cleavage of the indene double bond 1 and other isomeric forms such as the 2-methyl-3-phenyl indenes, 2-phenyl-3-phenyl indenes, 2-phenyl-3-methyl indenes, 1-phenyl-2-methyl-3-phenyl indenes to form the corresponding ketoaldehyde small molecule 2. The ketoaldehyde 2 and other polymorphic forms can be obtained with yields of 75% using batch chemical methods (Drawing 1) or with the use of a micro flow reactor (Drawing 5). The ketoaldehyde 2 is then combined with substituted amines to synthesize substituted 1,2,3,4-tetrahydroisoquinolines 3 in 28%-99% yields (Drawing 2).

The process of the present invention can synthesize 1,2,3,4-tetrahydroisoquinolines from many different substituted indenes that can be used as industrial chemicals or medicaments. They can be easily converted into salts that increase stability. The isoquinolines made using the process of the present invention have the general chemical structure I and II.

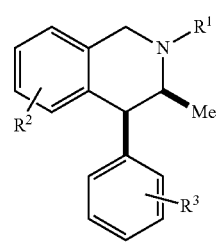

I

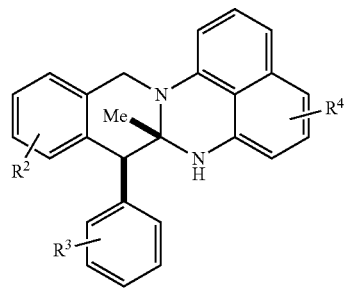

II

Wherein,
$R^1$=Me
  Et
  $CH_2(CH_2)_nCH_3$ $(n=1, 2, 3, 4, 5, 6, 7, 8, 9)$
  $(CH_2)_nC_6H_5$ $(n=1, 2, 3, 4, 5, 6, 7, 8, 9)$
  $C_6H_5$
  $C_6H_5(R^4)$
$R^2$=o-X, and/or m-X, and/or p-X, (X=F, Cl, Br, I)'
  o-$NO_2$, and/or m-$NO_2$, and/or p-$NO_2$'
  o-OMe, and/or m-OMe, and/or p-OMe,
  H
$R^3$=o-X, and/or m-X, and/or p-X, (X=F, Cl, Br, I),
  o-$NO_2$, and/or m-$NO_2$, and/or p-$NO_2$'
  o-OMe, and/or m-OMe, and/or p-OMe,
  H
$R^4$=o-X, and/or m-X, and/or p-X, (X=F, Cl, Br, I)
  o-$NO_2$, and/or m-$NO_2$, and/or p-$NO_2$
  o-OMe, and/or m-OMe, and/or p-OMe
  H Example 1,2,3,4-tetrahydroisoquinoline Synthesis 2-Methy-1-phenyl indene can be used in the process to be converted into a highly substituted 1,2,3,4-tetrahydroisoquinoline. To a stirred solution of 2-methyl-1-phenyl indene (400.0 mg, 1.940 mmol) in a solvent blend containing THF/$H_2O$ (12.0 mL) was added sodium periodate (3.31 g, 15.5 mmol) in water (4.0 mL) dropwise, forming a cloudy white solution. $K_2OsO_4$ (64.5 mg, 0.1940 mmol) was added forming a light tan solution that gradually turned light brown. The solution was stirred at room temperature for 20 h and monitored by TLC for the disappearance of indene. The reaction was quenched with water (10.0 mL) and stirred for 5 minutes and then ether was added (75.0 mL). The mixture was then washed with aqueous saturated $NaHCO_3$ solution (2×75 mL), water (10×50 mL), and brine (3×50 mL), and dried over $Na_2SO_4$ and evaporated in vacuo to afford the products as a brown-black oil. The crude oil was then quickly purified using column chromatography (10% ethyl acetate in hexanes) to yield 2 as a light brown oil (291.0 mg, 63% yield). IR (Thin Film): 3412, 3061, 3028, 2919, 2843, 2744, 1718, 1647, 1602, 1576, 1488, 1443, 1344, 1275, 1190, 1149, 1102, 1033, 951, 872 cm$^{-1}$. $^1$H NMR (400 MHz, CDCl$_3$) δ: 10.10 (1H, s), 7.80 (1H, m), 7.5-7.32 (9H, m), 7.25 (2H, d), 6.92 (1H, m), 6.20 (1H, s), 2.62 (3H, s) ppm. $^{13}$C NMR (300 MHz, CDCl$_3$) δ 206.3, 194.3, 140.6, 136.7, 136.4, 134.0, 133.6, 130.7, 130.2, 129.4, 128.0, 127.6, 61.5, 30.3 ppm. LRMS (EI+): m/z=238 (5), 236 (59), 222 (22), 195 (42), 178 (68), 165 (100), 152 (25), 139 (7), 115 (6), 89 (4), 63 (4). HRMS (EI+): m/z Calcd. for $C_{16}H_{12}O_2$: 236.0837. Found=236.0841.

Example 1

2-Butyl-3-methyl-4-phenyl-1,2,3,4-tetrahydroisoquinoline 9 was made using a stirred solution of ketoaldehyde 2 (50.0 mg, 0.251 mmol) in methanol (0.963 mL) in a 5.0 mL microwave vial at −78° C. was added a solvent blend dropwise consisting of butyl amine (24.8 μL, 0.251 mmol) dissolved in methanol (1.44 mL) and acetic acid (26.0 μL), forming a light yellow solution. NaBH$_3$CN (34.2 mg, 0.546 mmol) was added at −78° C. and stirred for 0.5 hours and then allowed to warm to room temperature. The initial light yellow/green solution turned light brown after an hour. The reaction was monitored by TLC and followed for the disappearance of the ketoaldehyde starting material. The reaction was then quenched with water (5.0 mL), saturated NaHCO$_3$ solution (5.0 mL), and then extracted with dichloromethane (3×20 mL). The organic extracts were dried over Na$_2$SO$_4$ and evaporated in vacuo to afford 9 as a light yellow oil (54.0 mg, 84% yield). Purification was not needed but in the case where the crude needed purification for some of the other products, column chromatography was used (0-10% ethyl acetate in hexanes). IR (Thin Film): 3059, 2952, 2790, 1697, 1597, 1487, 1445, 1370, 1241, 1174, 1093, 1031, 900, 709, 575 cm$^{-1}$. $^1$H NMR (400 MHz, CDCl$_3$) δ: 7.15 (8H, m), 6.98 (1H, d, J=7.5 Hz), 4.32 (1H, d, J=4.5 Hz), 3.93 (1H, d, J=15.5 Hz), 3.68 (1H, d, J=15.5 Hz), 3.16 (1H, m, J=7.0, 2.0 Hz), 2.75 (1H, dq, J=12.0, 7.0 Hz), 2.58 (1H, dq, J=12.0, 7.0 Hz), 1.52 (2H, m), 1.32 (2H, m), 0.92 (3H, t, J=7.0), 0.78 (3H, d, J=7.0 Hz) ppm. $^{13}$C NMR (300 MHz, CDCl$_3$) δ: 142.5, 136.9, 130.5, 129.5, 128.6, 127.7, 126.2, 126.2, 125.9, 125.7, 57.2, 53.6, 51.8, 50.8, 29.5, 20.6, 14.0, 11.0 ppm. LRMS (EI+): m/z=280 (1), 279 (15), 264 (95), 236 (90), 180 (91), 179 (100), 165 (34), 91 (2). HRMS (EI+): m/z Calcd. for C$_{20}$H$_{25}$N: 279.1987. Found: 279.1988.

Example 2

2-(4-Methoxyphenyl)-3-methyl-4-phenyl-1,2,3,4-tetrahydroisoquinoline 13 was made using a stirred solution of ketoaldehyde 2 (110.0 mg, 0.4621 mmol) in methanol (2.12 mL) in a 10.0 mL microwave vial at −78° C. was added a solvent blend dropwise consisting of p-anisidine (68.3 mg, 0.555 mmol) dissolved in methanol (2.65 mL) and acetic acid (38.7 μL), forming a light yellow solution. NaBH$_3$CN (75.5 mg, 1.201 mmol) was added at −78° C. and stirred for 0.5 hours and then allowed to warm to room temperature. The initial light yellow/green solution turned light brown after an hour. The reaction was monitored by TLC and followed for the disappearance of the ketoaldehyde starting material. The reaction was then quenched with water (5.0 mL), saturated NaHCO$_3$ solution (5.0 mL), and then extracted with dichloromethane (3×20 mL). The organic extracts were dried over Na$_2$SO$_4$ and evaporated in vacuo to afford 9 as a light yellow oil. The crude product was purified using silica gel column chromatography using an elution gradient of 10% EtOAc in hexanes. The fractions containing the desired product were collected and evaporated in vacuo to yield the pure 1,2,3,4-tetrahydroisoquinoline 13 as a light orange oil (113.0 mg, 75% yield). IR (Thin Film): 3059, 2976, 2837, 1501, 1444, 1385, 1292, 1240, 1168, 1033, 827, 762, 698 cm$^{-1}$. $^1$H NMR (400 MHz, CDCl$_3$) δ: 7.20 (9H, m), 6.96 (2H, dd, J=9.0, 2.0 Hz), 6.85 (2H, dd, J=9.0, 2.0 Hz), 4.53 (1H, d, J=5.5 Hz), 4.38 (2H, s), 4.23 (1H, dq, J=13.0, 6.5 Hz), 3.76 (3H, s), 0.9 (3H, d, J=6.5 Hz) ppm. $^{13}$C NMR (300 MHz, CDCl$_3$) δ: 153.9, 144.1, 141.8, 136.4, 134.7, 130.7, 129.6, 128.3, 126.9, 126.4, 126.3, 119.5, 114.7, 57.5, 55.8, 50.4, 48.4, 11.8 ppm. LRMS (EI+): m/z=329 (70), 314 (30), 312 (100), 297 (3), 269 (3), 195 (4), 194 (52), 180 (73), 179 (89), 165 (43), 149 (3), 77 (3). HRMS (EI+): m/z Calcd. for C$_{23}$H$_{23}$NO: 329.1780. Found: 329.1729.

Example 3

3-Methyl-2-(4-nitrophenyl)-4-phenyl-1,2,3,4-tetrahydroisoquinolin-3-ol 14 was made using a stirred solution of ketoaldehyde 2 (118.0 mg, 0.495 mmol) in methanol (2.27 mL) in a 10.0 mL microwave vial at −78° C. was added a solvent blend dropwise consisting of p-nitroaniline (82.1 mg, 0.5949 mmol) dissolved in methanol (2.844 mL) and acetic acid (41.5 μL), forming a light yellow solution. NaBH$_3$CN (81.0 mg, 1.289 mmol) was added at −78° C. and stirred for 5 hours and then allowed to warm to room temperature for 15 hours. The initial light yellow/green solution turned light brown after an hour. The reaction was monitored by TLC and followed for the disappearance of the ketoaldehyde starting material. The reaction was then quenched with water (5.0 mL), saturated NaHCO$_3$ solution (5.0 mL), and then extracted with dichloromethane (3×20 mL). The organic extracts were dried over Na$_2$SO$_4$ and evaporated in vacuo to afford 9 as a light yellow oil. The crude product was purified using silica gel column chromatography using an elution gradient of 10% EtOAc in hexanes that was gradually increased to 30% EtOAc in hexanes. The fractions containing the desired product were collected and evaporated in vacuo to yield the pure 1,2,3,4-tetrahydroisoquinoline as a light yellow oil in 28% yield as a 3:2 ratio of diastereomers. IR (Thin Film): 3395, 3056, 2980, 1718, 1631, 1597, 1490, 1445, 1381, 1226, 1181, 1107, 1060, 1012, 832, 701 cm$^{-1}$. $^1$H NMR (400 MHz, CDCl$_3$) δ: 7.33-7.00 (13H, m), 5.18 (0.4H, d, J=15.5 Hz isomer A), 5.13 (0.6H, d, J=15.5 Hz, isomer B), 4.98 (0.6H, d, J=15.5 Hz, isomer B), 4.89 (0.4H, d, J=15.5 Hz, isomer A), 4.13 (0.4H, s, isomer A), 3.98 (0.6H, s, isomer B), 2.54 (0.6H, s, isomer B), 2.30 (0.4H, s, isomer A), 1.47 (1.2H, s, isomer A), 1.24 (1.8H, s, isomer B) ppm. $^{13}$C NMR (300 MHz, CDCl$_3$) δ: 142.8, 140.0, 135.9, 135.1, 133.4, 132.4, 131.0, 130.7, 129.8, 129.4, 128.4, 128.4, 127.5, 127.2, 126.9, 126.9, 126.6, 126.5, 123.8, 123.6, 97.4, 96.5, 63.8, 62.6, 53.9, 53.0, 28.1, 26.5 ppm. LRMS (EI+): m/z=222 (41), 181 (41), 179 (100), 178 (73), 165 (7), 149 (8), 105 (3), 69 (37). HRMS (EI+): m/z Calcd. for C$_{22}$H$_{20}$N$_2$O$_2$ 222.1045 (-PhNO$_2$). Found=344.41.

Example 4

(3S,4S)-2-(4-Fluorophenyl)-3-methyl-4-phenyl-1,2,3,4-tetrahydroisoquinoline 15 was made using a stirred solution of ketoaldehyde 2 (75.0 mg, 0.313 mmol) in methanol (1.73 mL) in a 10.0 mL microwave vial at −78° C. was added a solvent blend dropwise consisting of p-fluoroaniline (30.0 μL, 0.313 mmol) dissolved in methanol (2.17 mL) and acetic acid (26.0 μL), forming a light yellow solution. NaBH$_3$CN (47.5 mg, 0.755 mmol) was added at −78° C. and stirred for 0.5 hours and then allowed to warm to room temperature. The solution turned light brown after an hour. The reaction was monitored by TLC and followed for the disappearance of the ketoaldehyde 2 starting material. The reaction was then quenched with water (5.0 mL), saturated NaHCO$_3$ solution (5.0 mL), and then extracted with dichloromethane (3×20 mL). The organic extracts were dried over Na$_2$SO$_4$ and evaporated in vacuo to afford 15 as a light brown oil (71.8 mg, 72% yield). The crude product was characterized without purification. IR (Thin Film): 3047, 3014, 2975, 2918, 2795, 1619, 1602, 1496, 1389, 1308, 1277, 1233, 1152, 1098, 1076, 1026, 986, 944, 880, 737, 659 cm$^{-1}$. $^1$H NMR (400 MHz, CDCl$_3$) δ: 7.38-7.22 (5H, m), 7.19-7.04 (2H, m), 6.98 (1H, m), 6.76-6.64 (1H, m), 4.60 (1H, d, J=5.0 Hz), 4.53 (1H, d, J=16.0 Hz), 4.41 (1H, d, J=16.0 Hz), 4.26 (1H, qd, J=6.5, 5.0 Hz), 0.91 (3H, d, J=6.5 Hz). $^{13}$C NMR (300 MHz, CDCl$_3$) δ: 158.6 (d) 146.4 (d, J=2.2 Hz), 146.6, 141.5, 136.1, 134.4, 130.7, 129.5, 128.4, 127.1, 126.6, 126.4, 126.4, 118.5 (d, J=7.4 Hz), 115.8, (d, J=22.1 Hz) 57.1, 50.3, 47.8, 11.5 ppm. LRMS (EI+): m/z=318 (3), 317 (44), 302 (11), 299 (20), 284 (12), 179 (100), 178 (66), 165 (43), 77 (3). FIRMS (EI+): Calcd. for C$_{22}$H$_{20}$NF: 317.1571. Found=317.1580.

Example 5

(7aS,8S)-7a-methyl-8-phenyl-7,7a,8,13-tetrahydroisoquinolino[2,3-a]perimidine 16 was made using a stirred solution of ketoaldehyde 2 (32.0 mg, 0.134 mmol) in methanol (0.577 mL) in a 5.0 mL microwave vial at −78° C. was added a solvent blend dropwise consisting of 1,8-diaminonapthalene (21.2 mg, 0.134 mmol) dissolved in methanol (0.724 mL) and acetic acid (10.5 µL, 0.161 mmol), forming a light yellow solution. NaBH$_3$CN (21.2 mg, 0.338 mmol) was added at −78° C. and stirred for 5 hours and then allowed to warm to room temperature for 15 hours. The initial cream solution turned light brown after an hour. The reaction was monitored by TLC and followed for the disappearance of the ketoaldehyde 2 starting material. The reaction was then quenched with water (5.0 mL), saturated NaHCO$_3$ solution (5.0 mL), and then extracted with dichloromethane (3×20 mL). The organic extracts were dried over Na$_2$SO$_4$ and evaporated in vacuo to afford 16 as a brown oil (23.9 mg, 49% yield). The crude product was characterized without purification. IR (Thin Film): 3367, 3058, 3019, 2969, 2918, 1697, 1585, 1496, 1412, 1375, 1294, 1250, 1166, 1104, 1073, 1031, 905, 810, 737, 698 cm$^{-1}$. $^1$H NMR (400 MHz, CDCl$_3$) δ: 7.40 (1H, t, J=8.0 Hz), 7.20 (13H, m), 6.74 (1H, d, J=8.0 Hz), 6.48 (1H, dd, J=6.0, 2.5 Hz), 5.10 (1H, d, J=16.0 Hz), 4.24 (1H, d, J=17.0 Hz), 4.14 (1H, s), 3.95 (1H, s), 1.4 (3H, s) ppm. $^{13}$C NMR (300 MHz, CDCl$_3$) δ: 142.2, 142.1, 138.6, 135.8, 134.4, 131.3, 130.2, 129.7, 128.6, 127.3, 127.2, 127.1, 126.9, 126.6, 118.3, 117.5, 114.2, 108.8, 104.5, 69.0, 56.8, 48.7, 22.8 ppm. LRMS (EI+): m/z=363 (5), 362 (13), 360 (8), 345 (4), 283 (4), 269 (4), 183 (11), 182 (100), 165 (4), 140 (4), 115 (3). HRMS (EI+): Calcd. for C$_{26}$H$_{22}$N$_2$: 362.1783. Found=362.1786.

Example 6 Using the Micro Flow Device Described (3S,4S)-2,3-dimethyl-4-phenyl-1,2,3,4-tetrahydroisoquinoline 6 can be made using the micro flow device disclosed (Drawing 5). Teflon tubing and fittings with an inner diameter of 0.15-0.2 mm was used leading into a pump from the chemical storage tank where the flow rate can be adjusted to the desired flow rate and controlled with a computer interface. The corresponding indene (110.0 mg) was dissolved in THF (1 mL) and placed in the indene storage container and the corresponding solvent pump adjusted to a flow rate of 0.5 mL/min. THF was added into the THF storage container and the corresponding solvent pump adjusted to a flow rate of 0.2 mL/min. Water was added into the water storage container and the corresponding solvent pump adjusted to a flow rate of 0.2 mL/min. A 0.1M solution containing potassium osmate in water was added into the osmium storage container and the corresponding pump adjusted to 0.1 mL/min. The oxidant storage container was prepared by adding a solution containing the sodium periodate dissolved in water and THF. The pump was adjusted to a rate of 0.5 mL/min. The reaction fluids were continuously pumped through the micro flow unit in the temperature regulating enclosure and allowed to flow through the micro flow coil at room temperature by controlling the temperature regulating enclosure. The back pressure was maintained at 30 PSI. The reaction fluid was pumped through the micro flow coil until the ketoaldehyde was detected and indene consumed by TLC or a detector such as a flow IR probe or $^1$HNMR spectrometer that was monitored with appropriate computer software. The completion of the product was carried out by allowing the reaction fluid to pass through the osmium scavenging column containing packed fine silica and an oxidant scavenging column to remove osmium and excess oxidant. The reaction fluid was passed through a microfiltration unit and collected in the ketoaldehyde product reservoir and the corresponding pump adjusted to a flow rate of 0.4 mL/min. The acetic acid storage container was filled with glacial acetic acid and the corresponding pump adjusted to a rate of 0.1 mL/min. The methanol storage container was filled with methanol and the flow rate adjusted to 0.4 mL/min. Finally, the amine storage container was filled with a solution containing the methylamine in methanol (1.0 eq.), sodium cyanoborohydride (2.1 eq.) and methanol and the flow rate adjusted to obtain an amine concentration of about 0.1M and the back pressure maintained at 30 PSI. The resultant solvent blend containing the ketoaldehyde was pumped through the micro flow coil for 0.5-1.5 hours or until the corresponding 1,2,3,4-tetrahydroisoquinoline was detected by TLC or a suitable detector such as such as a flow IR probe or $^1$HNMR spectrometer that can be monitored with appropriate computer software. If the product was not detected, the reaction fluid would continue to flow through the micro flow coil by controlling the multi temperature valves and the micro flow pump. The reaction stream containing the 1,2,3,4-tetrahydroisoquinoline was passed through an acid scavenging column to remove excess acetic acid and finally through a microfiltration unit to remove excess sodium cyanoborohydride. The reactor was flushed with 100 mL of THF and the final (3S,4S)-2,3-dimethyl-4-phenyl-1,2,3,4-tetrahydroisoquinoline 6 was collected in the collection container. The crude product was purified using silica gel column chromatography using an elution gradient of 10% EtOAc in hexanes that was gradually increased to 30% EtOAc in hexanes. The fractions containing the desired product were collected and evaporated in vacuo to yield the pure 1,2,3,4-tetrahydroisoquinoline 6 in (134.1 mg, 92% yield). IR (Thin Film): 3054, 2925, 2759, 1648, 1592, 1491, 1452, 1364, 1250, 1132, 1026, 907, 729, 757, 698 cm$^{-1}$. $^1$H NMR (400 MHz, CDCl$_3$) δ: 7.10 (9H, m), 6.95 (1H, d, J=7.5 Hz), 4.10 (1H, d, J=6.5 Hz), 3.98 (1H, d, J=16.5 Hz), 3.54 (1H, d, J=16.5 Hz), 3.54 (1H, d, J=16.5 Hz), 3.54 (1H, d, J=16.5 Hz), 2.86 (1H, dq, J=11.0, 6.5 Hz), 2.20 (3H, s), 0.9 (3H, d, J=6.5 Hz) ppm. $^{13}$C NMR (300 MHz, CDCl$_3$) δ: 143.1, 137.9, 135.0, 130.7, 129.9, 127.8, 126.3, 126.3, 126.1, 125.9, 59.3, 57.3, 51.4, 42.5, 14.7 ppm. LRMS (EI+): m/z=237 (7), 223 (8), 222 (50), 219 (32), 181(9), 180 (55), 179 (100), 178 (50), 165 (30). HRMS (EI+): Calcd. for C$_{17}$H$_{19}$N: 237.1517. Found=237.1525.

More examples of other 1,2,3,4-tetrahydroisoquinolines that have been made using the process of the present invention are shown in Table 1 and in Table 2. In addition, the examples are outlined in Drawing 3 and in Drawing 4.

TABLE 1

Examples of 1,2,3,4-tetrahydroisoquinolines that can be made using the process

| 1,2,3,4-tetrahydroisoquinoline | Name<br>Chemical Formula<br>Molecular Weight (g/mol) | Yield<br>d.e. |
|---|---|---|
| *(structure)* | (3S,4S)-2,3-dimethyl-4-phenyl-1,2,3,4-tetrahydroisoquinoline<br>$C_{17}H_{29}N$<br>237.35 | 92%<br>98:2 |
| *(structure)* | (3S,4S)-2-ethyl-3-methyl-4-phenyl-1,2,3,4-tetrahydroisoquinoline<br>$C_{18}H_{21}N$<br>251.37 | 62%<br>95:5 |
| *(structure)* | (3S,4S)-2-butyl-3-methyl-4-phenyl-1,2,3,4-tetrahydroisoquinoline<br>$C_{26}H_{25}N$<br>279.43 | 85%<br>98:2 |
| *(structure)* | (3S,4S)-3-methyl-2,4-diphenyl-1,2,3,4-tetrahydroisoquinoline<br>$C_{22}H_{21}N$<br>299.42 | 73-99%<br>98:2 |
| *(structure)* | (3S,4S)-2-benzyl-3-methyl-4-phenyl-1,2,3,4-tetrahydroisoquinoline<br>$C_{23}H_{23}N$<br>313.44 | 72%<br>95:5 |

TABLE 2

Examples of 1,2,3,4-tetrahydroisoquinolines that can be made using the process

| 1,2,3,4-tetrahydroisoquinoline | Name<br>Chemical Formula<br>Molecular Weight (g/mol) | Yield<br>d.e. |
|---|---|---|
| (structure) | (3S,4S)-3-methyl-2-phenethyl-4-phenyl-1,2,3,4-tetrahydroisoquinoline<br>$C_{24}H_{25}N$<br>327.47 | 47-99%<br>95:5 |
| (structure) | (3S,4S)-2-(4-methoxyphenyl)-3-methyl-4-phenyl-1,2,3,4-tetrahydroisoquinoline<br>$C_{23}H_{23}NO$<br>329.44 | 75%<br>98:2 |
| (structure) | (3S,4S)-3-methyl-2-(4-nitrophenyl)-4-phenyl-1,2,3,4-tetrahydroisoquinoline<br>$C_{22}H_{26}N_2O_2$<br>344.41 | 28%<br>70:30 |
| (structure) | (3S,4S)-2-(4-fluorophenyl)-3-methyl-4-phenyl-1,2,3,4-tetrahydroisoquinoline<br>$C_{22}H_{29}FN$<br>317.41 | 72%<br>91:10 |
| (structure) | (7aS,8S)-7a-methyl-8-phenyl-7,7a,8,13-tetrahydroisoquinoline[2,3-a]perimidine<br>$C_{26}H_{22}N_2$<br>362.48 | 49%<br>98:2 |

DETAILED DESCRIPTION OF THE EMBODIMENTS OF THE INVENTION

In one embodiment of the process in the present invention, the process is complete within 2-20 hours, providing several advantages over other processes that cleave an alkene or indene double bond. Time is saved because the useful chemical products are obtained within hours as opposed to days. Other processes disclosed in the art require longer reaction times and more expensive chemicals to use. These processes can involve stirring the reaction for several days which can be problematic due to the production of unwanted waste chemicals or chemical decomposition that can lead to lower process efficiencies.

In a second embodiment of the present invention, the process is successful at using several different substituted indenes including the 2- and 3-substituted indenes which pose challenges (JOC 1981, 46, 5000-5003). Methods only exist to make the unsaturated isoquinoline ring system which is different from the 1,2,3,4-tetrahydroisoquinolines ring system. The 1,2,3,4-tetrahydroisoquinoline ring system is a more versatile chemical that is used in medicaments and is found in larger quantities in biomass. Some examples of 1,2,3,4-tetrahydroisoquinolines that are naturally occurring are Carnegine and Laudanine (Drawing 2). In addition, the process of the present invention is advantageous because a large library of 1,2,3,4-tetrahysroisoquinolines can be made where other processes disclosed in the art can only make isoquinoline. In addition, the process of the present invention can make starting materials that can be oxidized to form other chemicals such as isoquinolines.

In a third embodiment of the present invention, the 1,2,3,4-tetrahydroisoquinolines are obtained in high selectivity which is very difficult to obtain and challenging for methods to achieve. Other reported methods that use ozone to make isoquinoline are less selective and lead to more waste from the formation of unwanted products such as carboxylic acids and other unstable peroxides. These methods do not provide control over selectivity of the diastereomers that can be formed. In addition, these methods provide isoquinolines that do not have diastereomers leading to less variability of the final products that can be made.

Yet another embodiment of the process of the present invention is that ozone does not have to be used providing greater production safety. Ozone is a toxic gas that is explosive under certain conditions which becomes a safety concern during its use in chemical manufacturing and research and development activities. The process detailed in the present invention does not use ozone eliminating the explosion hazard, providing another advantage for the present invention. The solid chemical component used in the process is not explosive and provides several advantages of higher selectivity and safety by eliminating this risk.

Another embodiment of the present invention involves the use of a micro flow reactor to provide a greater degree of control and selectivity when making 1,2,3,4-tetrahydroisoquinolines. The micro flow reactor disclosed allows for precise computerized control of the reaction by regulating flow rates, concentrations of chemicals, temperatures, and residence times providing superior advantages over batch methods that do not have such precise control. The present invention discloses a micro flow reactor to provide this superior control of reaction parameters.

Another embodiment of the process of the present invention discloses a vessel that can be a micro flow reactor that has the ability to use osmium in both anaerobic and aerobic atmospheres. Such a micro flow reactor provides a safer way to control chemical manufacturing when using osmium and its salts. The ability to use osmium in a safer way provides advantages over conventional ways to use osmium because there is a higher level of containment and control of use by personnel when using osmium for chemical and pharmaceutical manufacturing. The micro flow reactor disclosed in the present invention provides additional safety and chemical control when using osmium to make chemicals.

Another embodiment of the present invention involves the high degree of stereoselectivity that is obtained in the final 1,2,3,4-tetrahydroisoquinoline products when using the process of the present invention. The 1,2,3,4-tetrahydroisoquinolines are obtained in high diastereomeric excess of greater than 98:2 for the syn product. This diastereoselectivity is very desirable when developing medicaments because of improved bioavailability and metabolic clearance. This process provides greater utility and is advantageous when manufacturing 1,2,3,4-tetrahydroisoquinolines because the diastereoselectivity can be controlled, producing less waste byproducts.

Another embodiment of the process of the present invention is the ability to use many solvent blends that are different from each other and are cost efficient chemicals that can be purchased from major chemical suppliers. The solvent blend contains an organic solvent and water forming a solvent blend with better properties that provide increased process efficiency. In addition, one of the solvent blends contains methanol and amine or methanol and acetic acid that is used in the process. Such solvent blends are inexpensive, less flammable, less explosive, and less toxic providing advantages for the user of the process of the present invention. The solvent blends used in the process of the present invention provide a better solvent that can be used advantageously because of the added safety that is provided because water is used in the solvent blend. Further, water is less expensive and less toxic than other solvents that are used in other chemical processes.

In another embodiment of the present invention, a second solvent blend is used in the process containing methanol. Methanol is combined with acetic acid and the amine providing a safer blend to be used in the process and more convenient to use. Methanol has a low cost for use and is used in a solvent blend disclosed. The low operational costs and increase in safety of the solvent blends disclosed in the process of the present invention provides a benefit. In addition, methanol is available from chemical suppliers in large quantities.

Another embodiment of the process of the present invention is the ability to use chemicals which are commodity chemicals. The chemicals that are used for this process to make 1,2,3,4-tetrahydroisoquinolines are very low cost commodity chemicals that can be purchased on multi ton scales. The process of the present invention can make 1,2,3,4-tetrahydroisoquinolines from C9 and higher feedstocks that include indenes that are found in coal tar and bitumen. These feedstock chemicals are inexpensive and easily purchased from chemical and petroleum industries. The process of the present invention provides a more robust industrial scale process to manufacture 1,2,3,4-tetrahydroisoquinolines because the chemicals used in the process are very abundant commodity chemicals. The use of very inexpensive starting chemicals in a large industrial scale chemical manufacturing process is very advantageous because of a larger profit and return on investment to be made from using the process.

Yet another embodiment of the process of the present invention involves the use of low temperatures to make the 1,2,3,4-tetrahydroisoquinolines. The use of lower operating temperatures in a chemical process is advantageous because of the energy savings and the costs associated with heating materials within a reactor. Lower operating temperatures provide lower operational costs because less energy is needed for heating large chemical reactors. These lower operating temperatures provide a more economically feasible process. The process of the present invention uses temperatures below 25° C. providing cost reductions for the user of the process. Therefore, the process can operate in colder environments and lower operational cost.

Another embodiment of the process of the present invention involves the multitude of chemicals that can be generated. Thousands of chemicals can be made that have different properties such as medicaments, detergents, corrosion inhibitors, disinfectants, oil field chemicals, fracking additives, viscosifiers, hydrate inhibitors, and other chemicals. Such a process to make 1,2,3,4-tetrahydroisoquinolines does not exist to provide this multitude of chemicals having as many uses. Therefore, a new process is available for one skilled in the art to make new 1,2,3,4-tetrahydroisoquinolines.

Another embodiment of the process of the present invention involves the use of metal chemicals that can be used as catalysts, additives or stoichiometric reagents to make 1,2,3,4-tetrahydroisoquinolines. Osmium and its salts can be used in different forms to make the ketoaldehyde that is used in the process of the present invention to make 1,2,3,4-tetrahydroisoquinolines. Osmium salts have many advantages because they can be recycled and can be used in water and organic solvents that can be problematic for other chemicals. Osmium can be purchased from chemical suppliers providing a chemical that is easy to obtain. In addition, heating is not required with the use of osmium because of the unique reactivity this chemical has. The low temperature operation from the use of osmium provides advantages and benefits from lower operational costs.

Another embodiment of the process of the present invention involves not having to use phosphate buffer. Phosphate buffer is not needed to form the 1,2,3,4-tetrahydroisoquinolines compounds. The process described does not use phosphate buffer providing an additional benefit because phosphate buffer is not needed. The process of the present invention has advantages by not having to use phosphate buffer.

BRIEF DESCRIPTION OF THE DRAWINGS

The embodiments of the present invention will now be described by reference using the drawings where reference numerals are used to describe the elements in the drawings.

DESCRIPTION OF THE DRAWINGS

Figure 1:
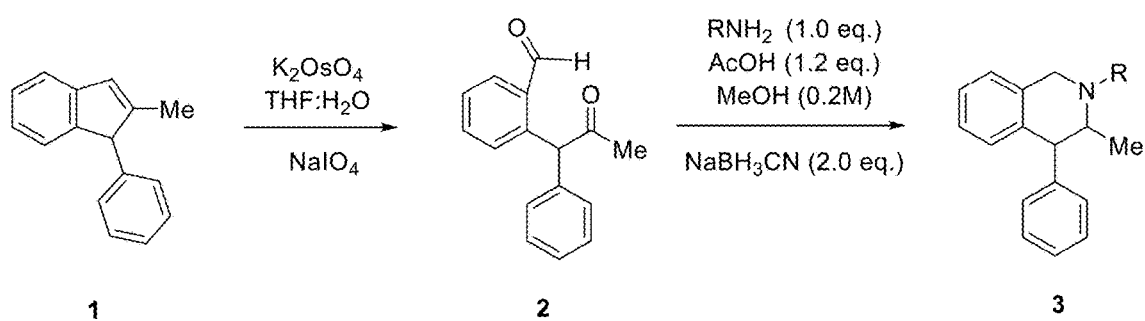
Figure 5:
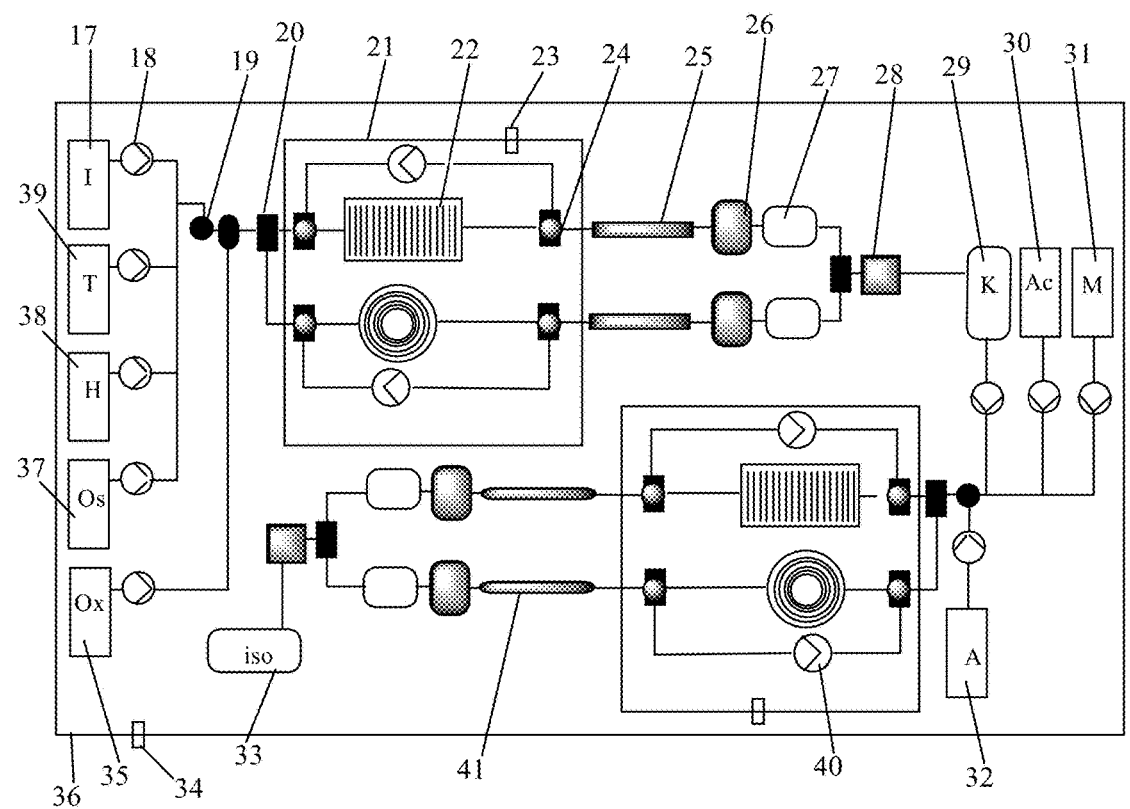
Figure 6:
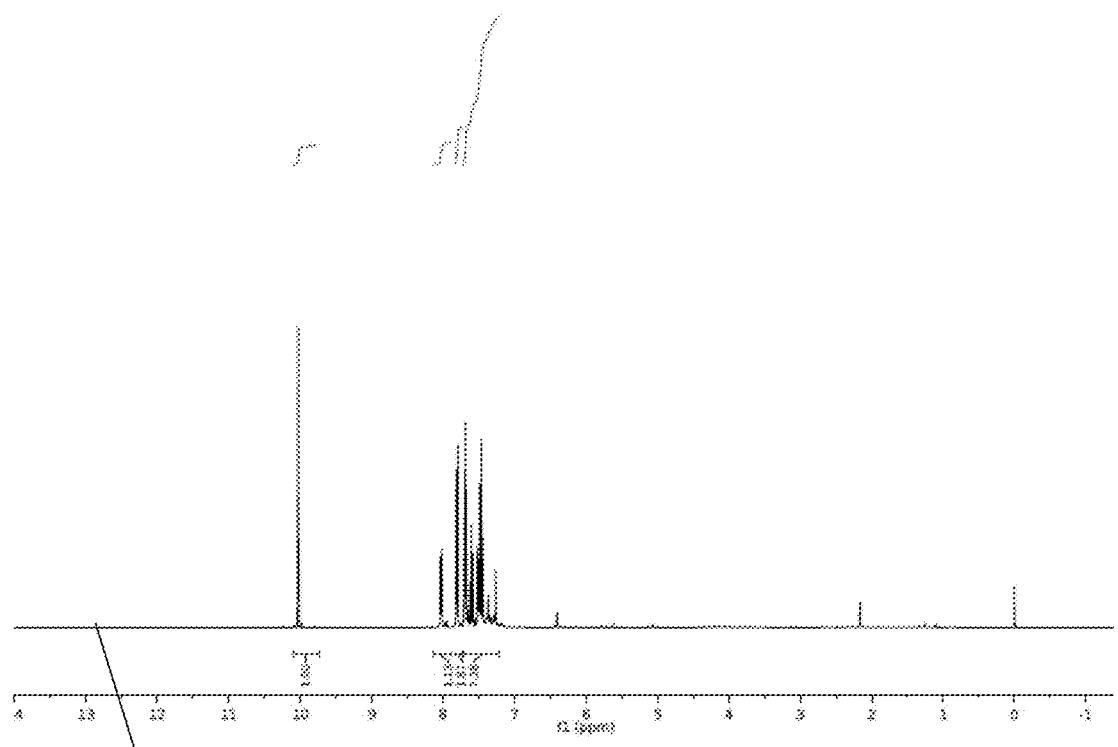
Figure 7:
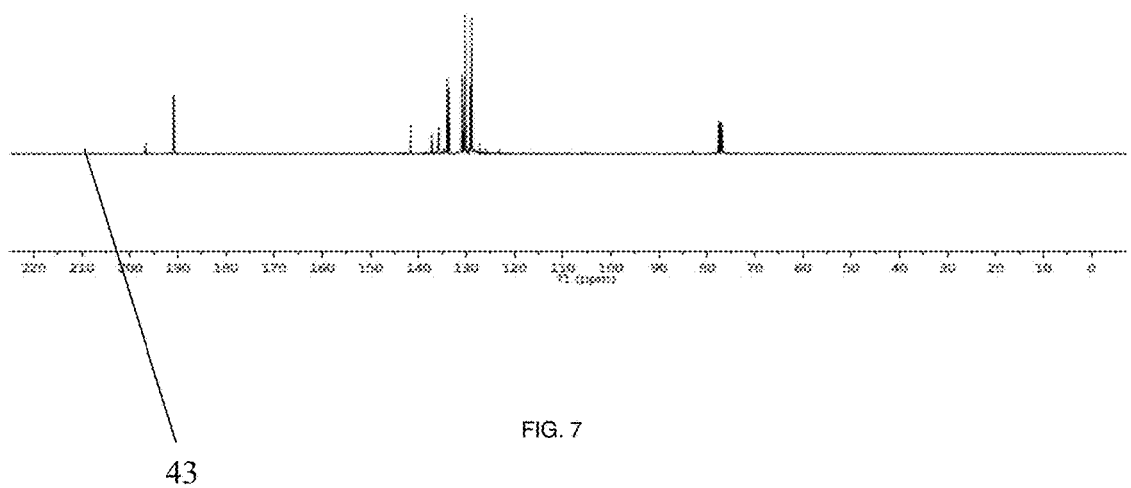
Figure 8:
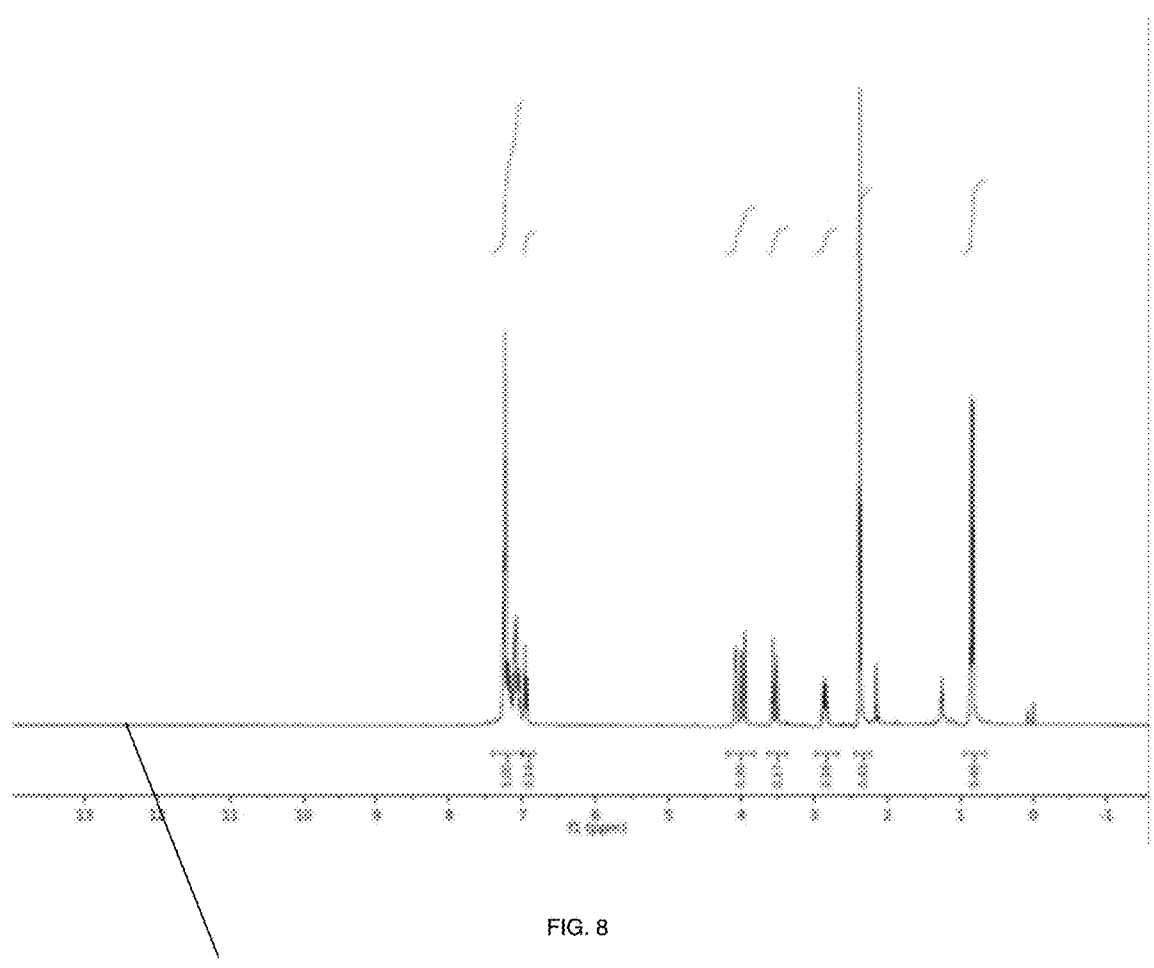
Figure 9:
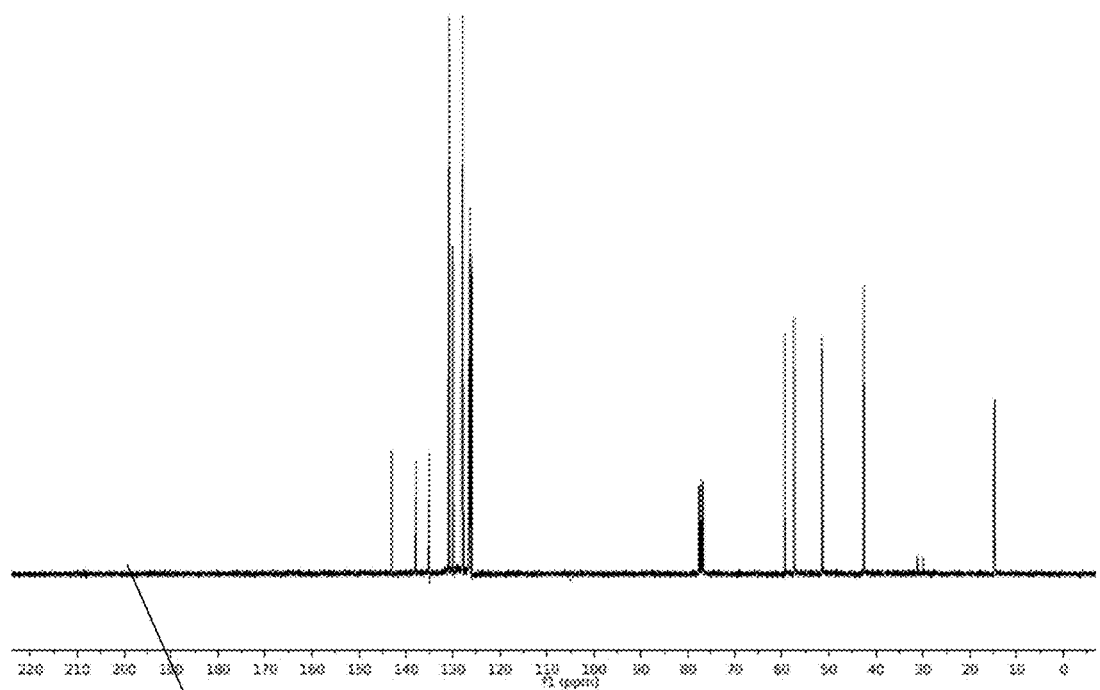
Figure 10:
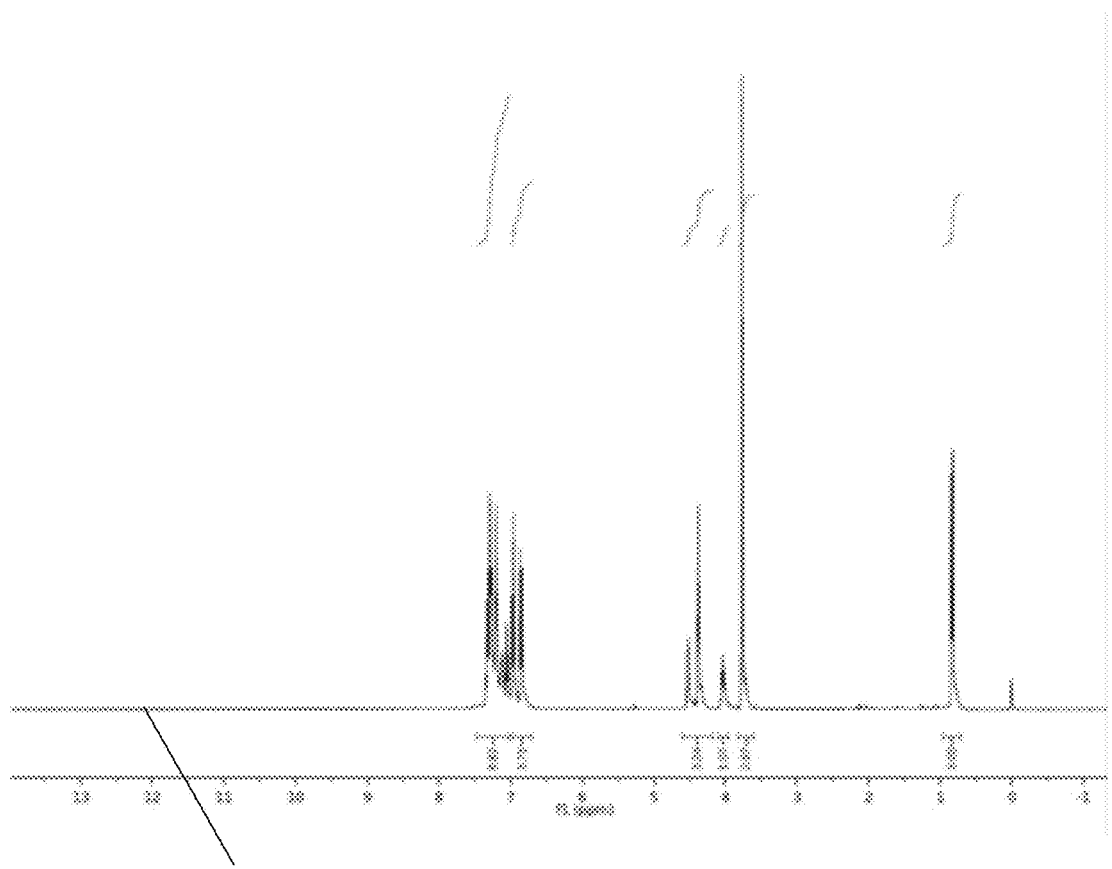
Figure 11:
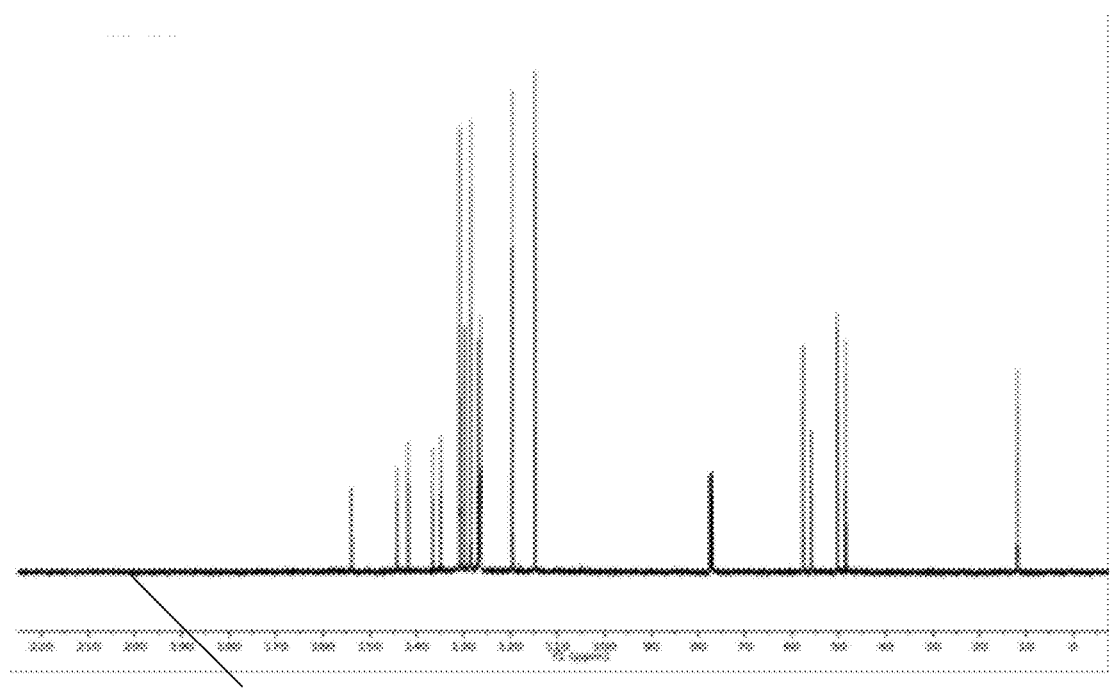
Figure 12:
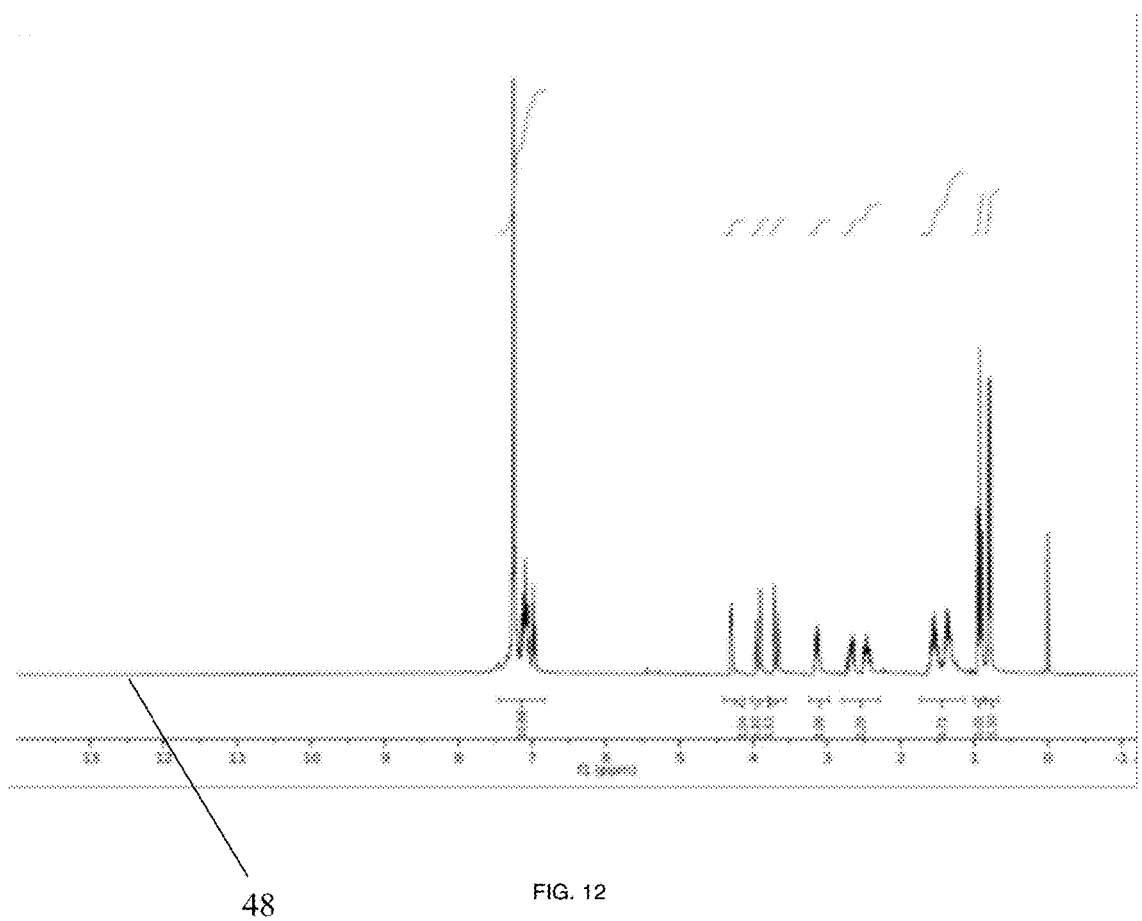
Figure 13:
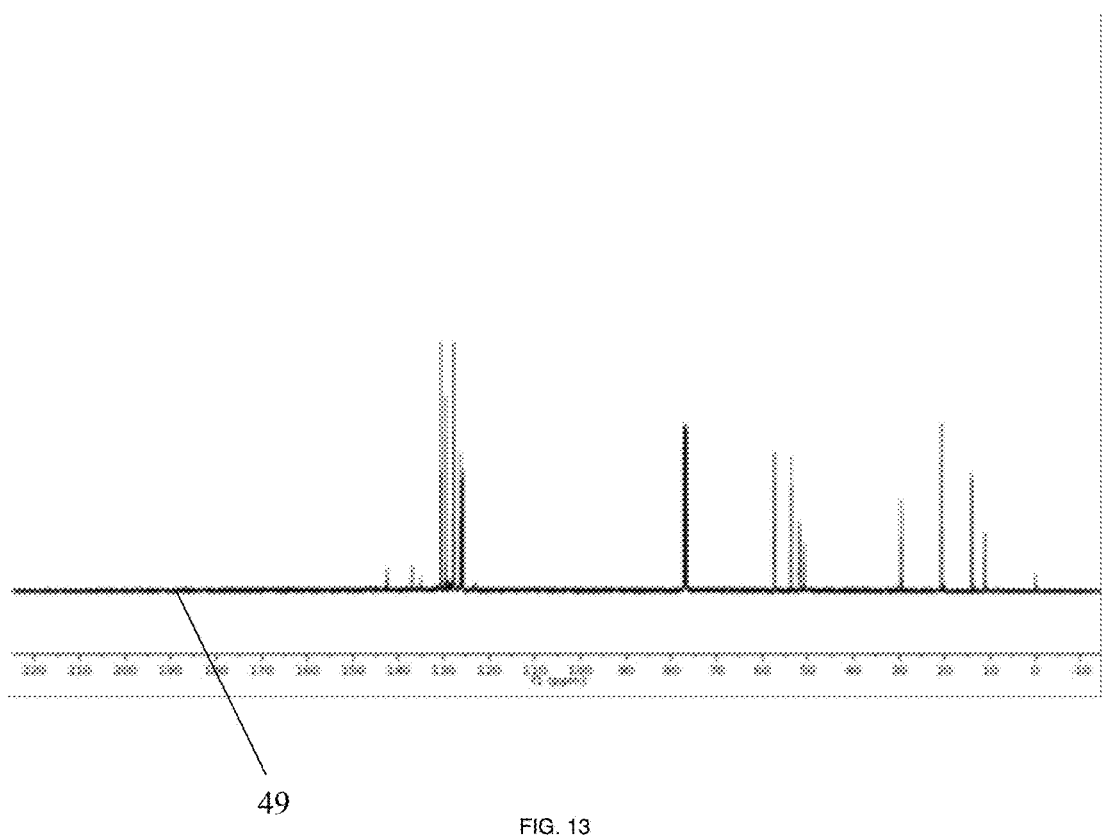
Figure 14:
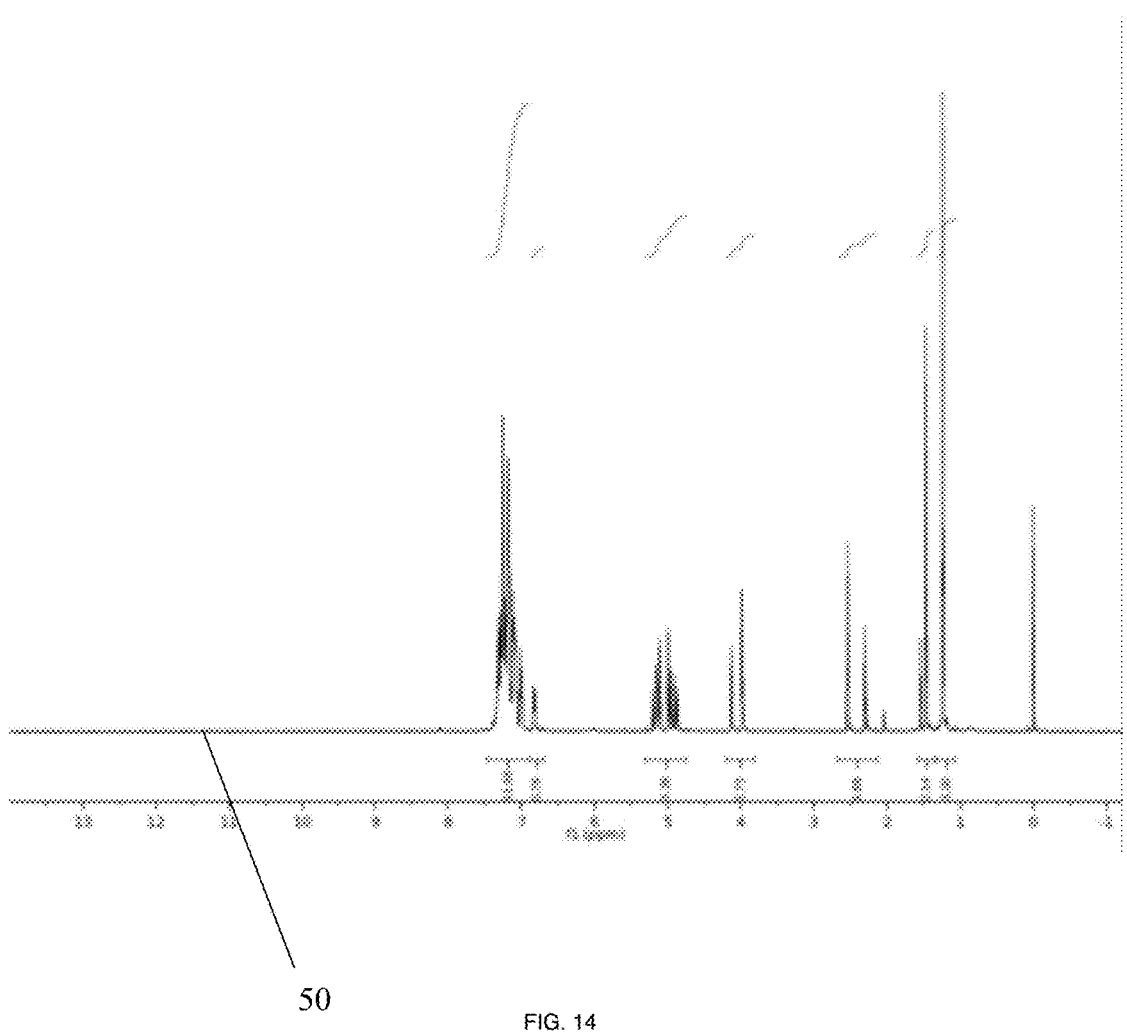
Figure 15:
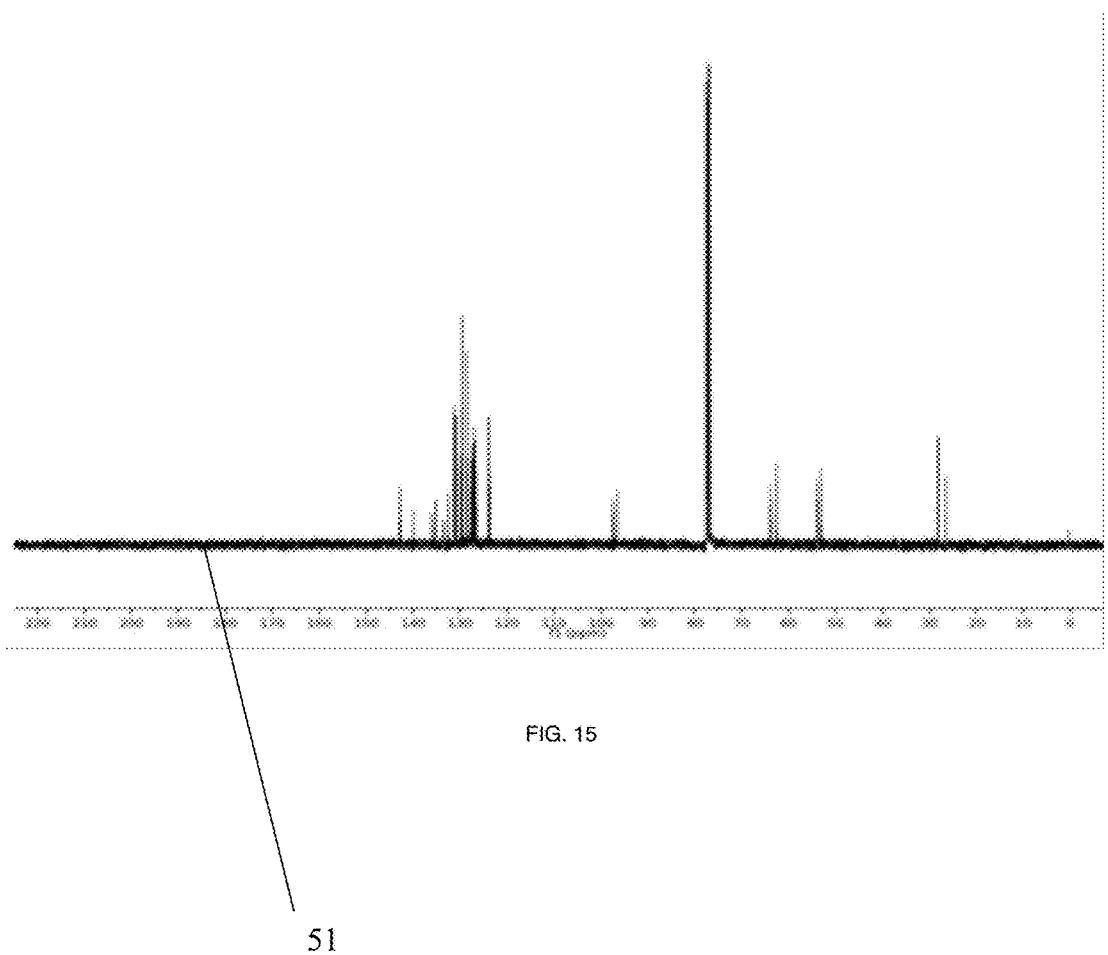
Figure 16:
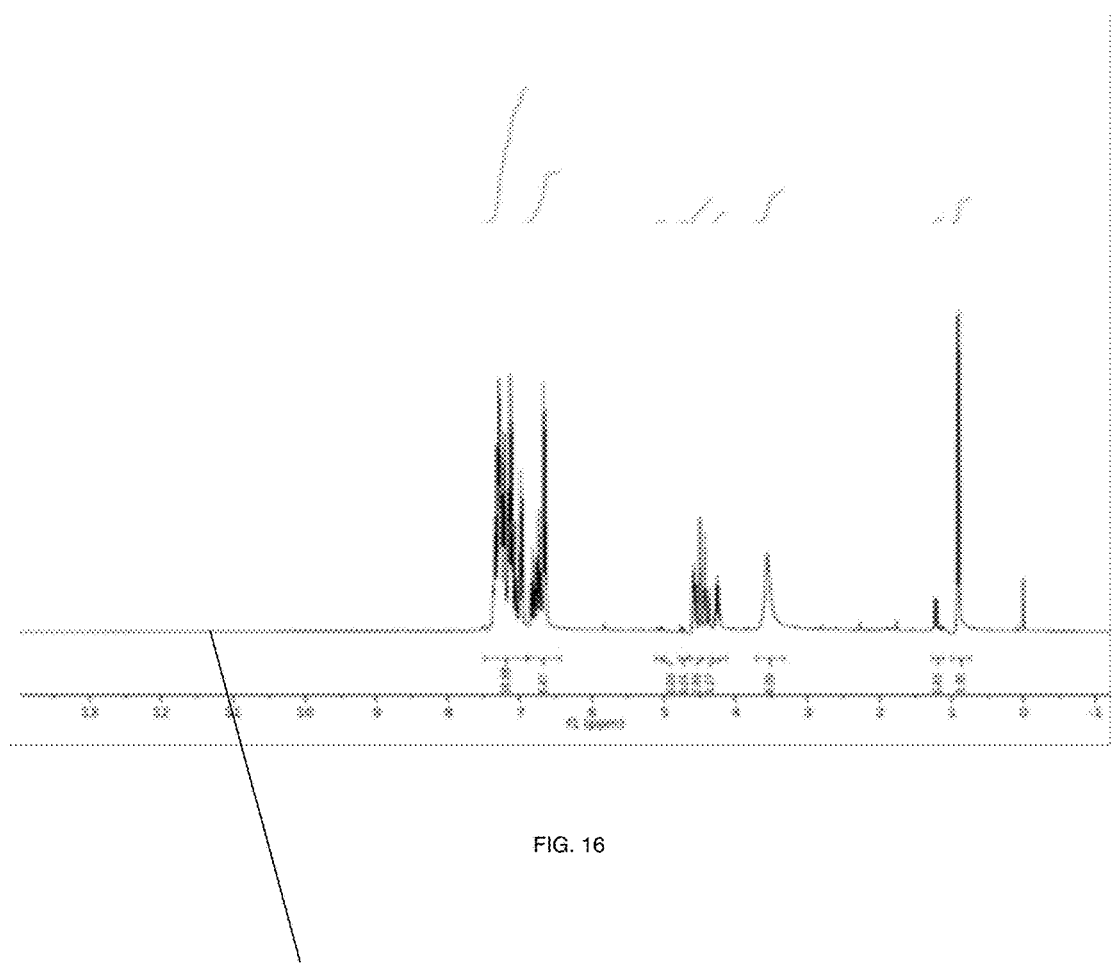
Figure 17:
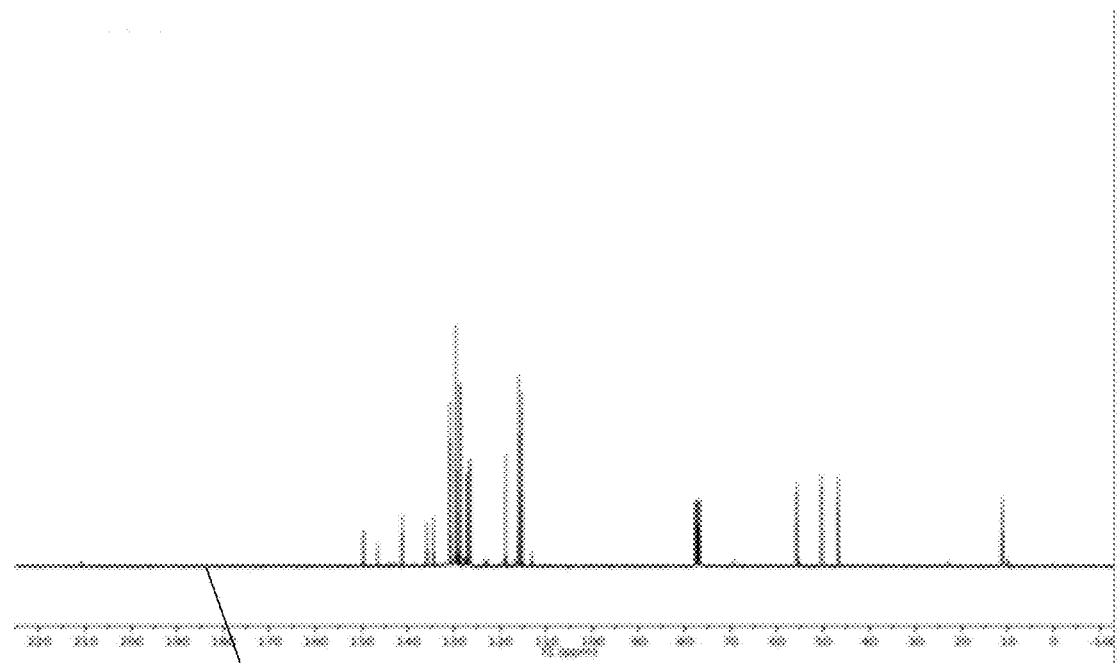
Figure 18:
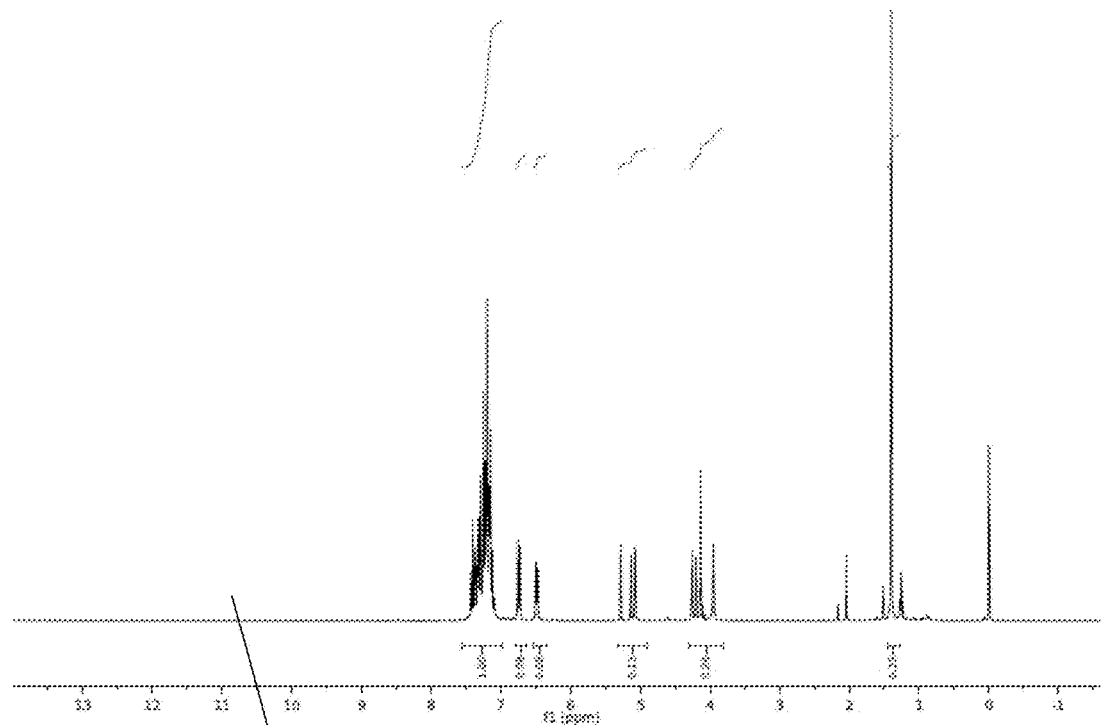
Figure 19:
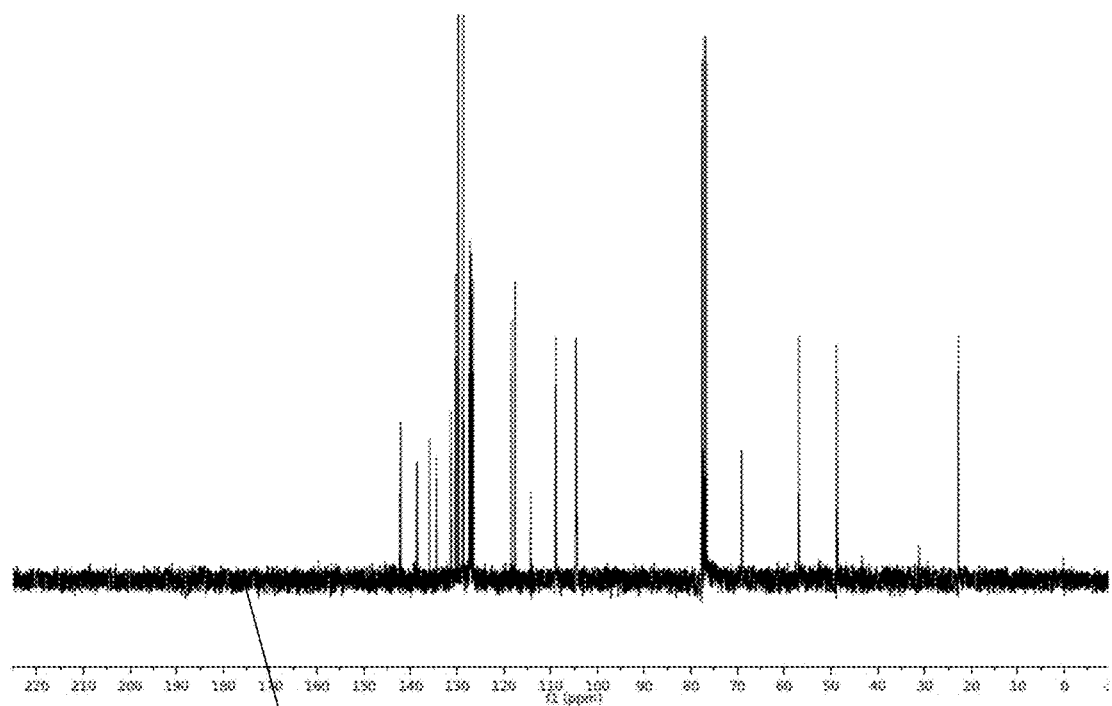
Figure 20:
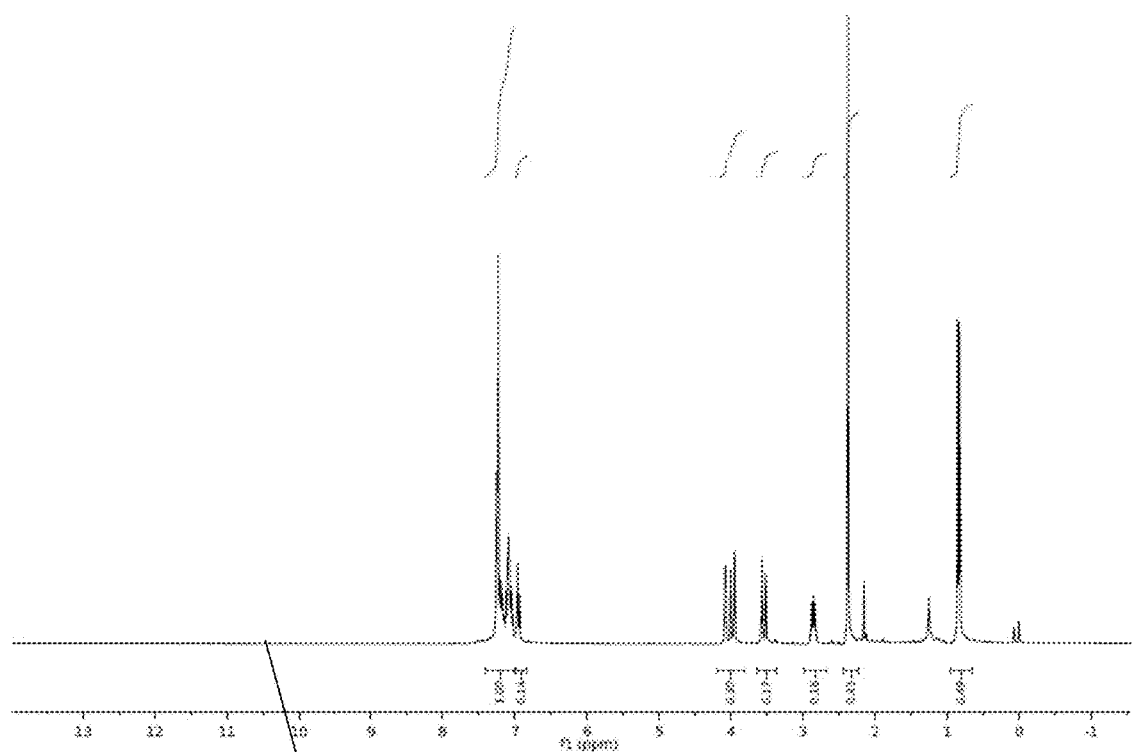
Figure 21:
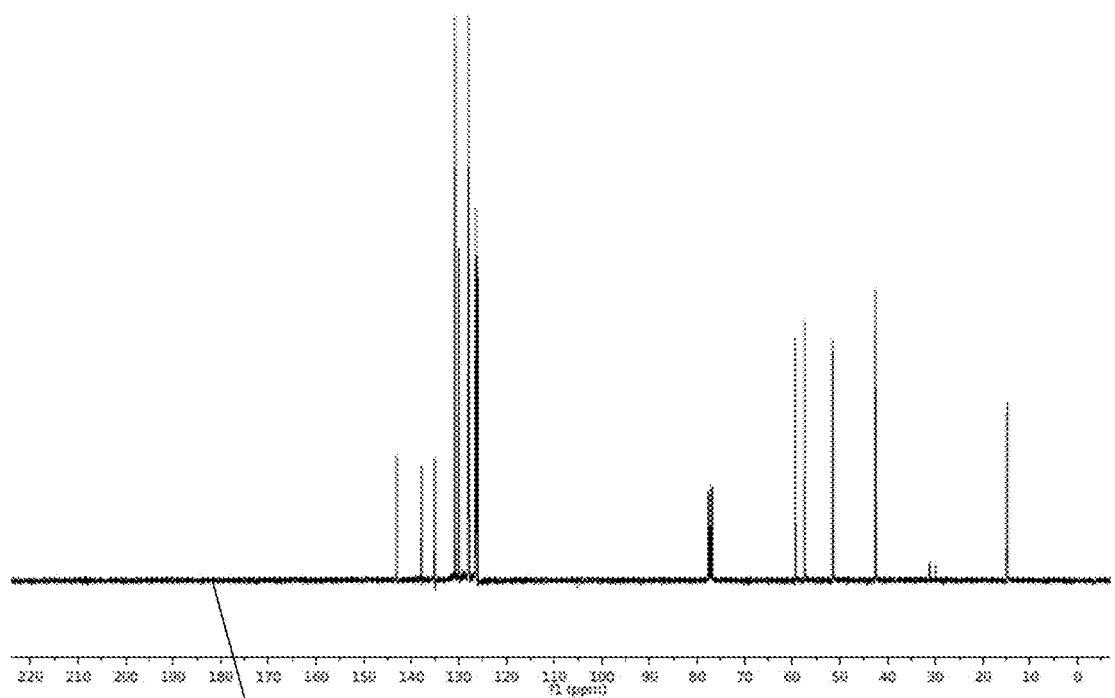

Drawing 1 shows the process of the present invention that uses methyl and phenyl indenes to make 1,2,3,4-tetrahydroisoquinolines.

Drawing 2 shows a substituted 1,2,3,4-tetrahydroisoquinoline and naturally occurring 1,2,3,4-tetrahydroisoquinolines.

Drawing 3 shows the different 1,2,3,4-tetrahydroisoquinolines that can be made using the process of the present invention.

Drawing 4 shows more examples of the different 1,2,3,4-tetrahydroisoquinolines that can be made using the process of the present invention.

Drawing 5 shows the micro flow reactor used to make 1,2,3,4-tetrahydroisoquinoline.

Drawing 6 shows the $^1$HNMR spectrum of the ketoaldehyde 2 in CDCl$_3$ with Tetramethylsilane.

Drawing 7 shows the $^{13}$CNMR of the ketoaldehyde 2 in CDCl$_3$ with TMS.

Drawing 8 shows the $^1$HNMR of (3S,4S)-2,3-dimethyl-4-phenyl-1,2,3,4-tetrahydroisoquinoline in CDCl$_3$ with TMS.

Drawing 9 shows the $^{13}$CNMR of (3S,4S)-2,3-dimethyl-4-phenyl-1,2,3,4-tetrahydroisoquinoline in CDCl$_3$ with TMS.

Drawing 10 shows the $^1$HNMR of (3S,4S)-2-(4-methoxyphenyl)-3-methyl-4-phenyl-1,2,3,4-tetrahydroisoquinoline in CDCl$_3$ with TMS.

Drawing 11 shows the $^{13}$CNMR of (3S,4S)-2-(4-methoxyphenyl)-3-methyl-4-phenyl-1,2,3,4-tetrahydroisoquinoline in CDCl$_3$ with TMS.

Drawing 12 shows the $^1$HNMR of (3S,4S)-2-butyl-3-methyl-4-phenyl-1,2,3,4-tetrahydroisoquinoline in CDCl$_3$ with TMS.

Drawing 13 shows the $^{13}$CNMR of (3S,4S)-2-butyl-3-methyl-4-phenyl-1,2,3,4-tetrahydroisoquinoline in CDCl$_3$ with TMS.

Drawing 14 shows the $^1$HNMR of (3S,4S)-3-methyl-2-(4-nitrophenyl)-4-phenyl-1,2,3,4-tetrahydroisoquinoline in CDCl$_3$ with TMS.

Drawing 15 shows the $^{13}$CNMR of (3S,4S)-3-methyl-2-(4-nitrophenyl)-4-phenyl-1,2,3,4-tetrahydroisoquinoline in CDCl$_3$ with TMS.

Drawing 16 shows the $^1$HNMR of (3S,4S)-2-(4-fluorophenyl)-3-methyl-4-phenyl-1,2,3,4-tetrahydroisoquinoline in CDCl$_3$ with TMS.

Drawing 17 shows the $^{13}$CNMR of (3S,4S)-2-(4-fluorophenyl)-3-methyl-4-phenyl-1,2,3,4-tetrahydroisoquinoline in CDCl$_3$ with TMS.

Drawing 18 shows the $^1$HNMR of 16 (7aS,8S)-7a-methyl-8-phenyl-7,7a,8,13-tetrahydroisoquinolino[2,3-a]perimidine in CDCl$_3$ with TMS.

Drawing 19 shows the $^{13}$CNMR of 16 (7aS,8S)-7a-methyl-8-phenyl-7,7a,8,13-tetrahydroisoquinolino[2,3-a]perimidine CDCl$_3$ with TMS.

Drawing 20 shows the $^1$HNMR of (3S,4S)-2,3-dimethyl-4-phenyl-1,2,3,4-tetrahydroisoquinoline in CDCl$_3$ with TMS.

Drawing 21 shows the $^{13}$CNMR of (3S,4S)-2,3-dimethyl-4-phenyl-1,2,3,4-tetrahydroisoquinoline in CDCl$_3$ with TMS.

LEGEND FOR DRAWING REFERENCE LABELS 1 2-Methyl-1-phenylindene
2 Ketoaldehyde
3 1,2,3-methyl-4-phenyltetrahydroisoquinoline
4 Carnegine
5 Laudanine
6 (3S,4S)-2-3-dimethyl-4-phenyl-1,2,3,4-tetrahydroisoquinoline
7 (3S,4S)-2,3-dimethyl-4-phenyl-1,2,3,4-tetrahydroisoquinoline
8 (3S,4S)-2-ethyl-3-methyl-4-phenyl-1,2,3,4-tetrahydroisoquinoline
9 (3S,4S)-2-butyl-3-methyl-4-phenyl-1,2,3,4-tetrahydroisoquinoline
10 (3S,4S)-3-methyl-2,4-diphenyl-1,2,3,4-tetrahydroisoquinoline 11 (3S,4S)-2-benzyl-3-methyl-4-phenyl-1,2,3,4-tetrahydroisoquinoline
12 (3S,4S)-3-methyl-2-phenethyl-4-phenyl-1,2,3,4-tetrahydroisoquinoline
13 (3S,4S)-2-(4-methoxyphenyl)-3-methyl-4-phenyl-1,2,3,4-tetrahydroisoquinoline
14 (3S,4S)-3-methyl-2-(4-nitrophenyl)-4-phenyl-1,2,3,4-tetrahydroisoquinoline
15 (3S,4S)-2-(4-fluorophenyl)-3-methyl-4-phenyl-1,2,3,4-tetrahydroisoquinoline
16 (7aS,8S)-7a-methyl-8-phenyl-7,7a,8,13-tetrahydroisoquinolino[2,3-a]perimidine
17 Indene or alkene starting material storage tank
18 Micro flow pump
19 Mixing unit
20 Switching valve
21 Temperature regulating enclosure
22 Microreactor unit containing channels and grooves
23 Aerobic/anaerobic atmosphere valve to temperature regulating enclosure
24 Multi temperature valve
25 Osmium scavenging column
26 Scavenging column
27 Microfiltration unit
28 Detector
29 Ketoaldehyde storage tank
30 Acetic acid storage tank
31 Methanol storage tank
32 Amine storage tank
33 1,2,3,4-tetrahydroisoquinoline product storage tank
34 Aerobic/anaerobic atmosphere valve to micro flow reactor enclosure
35 Oxidant storage tank
36 Flow Reactor Closure to control anaerobic/aerobic atmosphere
37 Osmium storage tank
38 Water storage tank
39 Tetrahydrofuran storage tank
40 Micro flow pump
41 Base scavenging column
42 $^1$HNMR of ketoaldehyde in CDCl$_3$ with TMS
43 $^{13}$CNMR of ketoaldehyde in CDCl$_3$ with TMS
44 $^1$HNMR of (3S,4S)-2,3-dimethyl-4-phenyl-1,2,3,4-tetrahydroisoquinoline CDCl$_3$ with TMS
45 $^{13}$CNMR of (3S,4S)-2,3-dimethyl-4-phenyl-1,2,3,4-tetrahydroisoquinoline in CDCl$_3$ with TMS
46 $^1$HNMR of (3S,4S)-2-(4-methoxyphenyl)-3-methyl-4-phenyl-1,2,3,4-tetrahydroisoquinoline in CDCl$_3$ with TMS
47 $^{13}$CNMR of (3S,4S)-2-(4-methoxyphenyl)-3-methyl-4-phenyl-1,2,3,4-tetrahydroisoquinoline in CDCl$_3$ with TMS
48 $^1$HNMR of (3S,4S)-2-butyl-3-methyl-4-phenyl-1,2,3,4-tetrahydroisoquinoline CDCl$_3$ with TMS
49 $^{13}$CNMR of (3S,4S)-2-butyl-3-methyl-4-phenyl-1,2,3,4-tetrahydroisoquinoline in CDCl$_3$ with TMS
50 $^1$HNMR of (3S,4S)-3-methyl-2-(4-nitrophenyl)-4-phenyl-1,2,3,4-tetrahydroisoquinoline in CDCl$_3$ with TMS
51 $^{13}$CNMR of (3S,4S)-3-methyl-2-(4-nitrophenyl)-4-phenyl-1,2,3,4-tetrahydroisoquinoline in CDCl$_3$ with TMS
52 $^1$HNMR of (3S,4S)-2-(4-fluorophenyl)-3-methyl-4-phenyl-1,2,3,4-tetrahydroisoquinoline in CDCl$_3$ with TMS
53 $^{13}$CNMR of (3S,4S)-2-(4-fluorophenyl)-3-methyl-4-phenyl-1,2,3,4-tetrahydroisoquinoline in CDCl$_3$ with TMS
54 $^1$HNMR of (7aS,8S)-7a-methyl-8-phenyl-7,7a,8,13-tetrahydroisoquinolino[2,3-a]perimidine in CDCl$_3$ with TMS.
55 $^{13}$CNMR of 16 (7aS,8S)-7a-methyl-8-phenyl-7,7a,8,13-tetrahydroisoquinolino[2,3-a]perimidine CDCl$_3$ with TMS.
56 $^1$HNMR of (3S,4S)-2,3-dimethyl-4-phenyl-1,2,3,4-tetrahydroisoquinoline in CDCl$_3$ with TMS.
57 $^{13}$CNMR of (3S,4S)-2,3-dimethyl-4-phenyl-1,2,3,4-tetrahydroisoquinoline in CDCl$_3$ with TMS.

The invention claimed is:

1. A chemical process that uses a solvent blend, an oxidant, an indene, and a metal salt to form 1,2,3,4-tetrahydroisoquinolines by oxidative cleavage of the indene using a reaction vessel.

2. The chemical process of claim 1 wherein the oxidant comprises a mixture containing a periodate salt oxidant comprising sodium periodate.

3. The chemical process of claim 1 wherein the oxidant comprises a mixture of oxidizing chemicals with oxidizing properties similar to a periodate salt oxidant.

4. The chemical process of claim 1 wherein the indene comprises one of a coal tar and a petroleum-derived chemical comprising methyl and phenyl substituted isomers.

5. The chemical process of claim 1 wherein the metal salt comprises an osmium salt comprising potassium osmate.

6. The chemical process of claim 1 wherein the solvent blend comprises a water-containing solvent system that contains an organic solvent.

7. The chemical process of claim 1 wherein the chemical process is used upgrading of petroleum, coal tar and coal oil products that contain indene in mass quantities ranging from 0.0010%-99.9% per gram of the specified petroleum or coal tar or coal oil starting material.

8. The chemical process of claim 1 wherein the chemical process is used to make 1,2,3,4-tetrahydroisoquinolines using 2-methyl-1-phenyl indenes with chemical yields ranging from 0.0100%-99.99%.

9. The chemical process of claim 1 wherein the reaction vessel is capable of being sealed and comprises one of a batch reactor and a micro flow reactor that holds an anaerobic or an aerobic atmosphere.

10. The chemical process of claim 9 wherein the micro flow reactor comprises one of a microreactor, a flow reactor and a flow apparatus comprising pre-fabricated channels with dimensions of breadth and height ranging from 1 micrometer to 200 micrometers.

11. The chemical process of claim 9 wherein the micro flow reactor is configured to pass a chemical reaction fluid inside the channels—with distances travelled by the chemical reaction fluid ranging from 1 mm to 1000 meters.

12. The chemical process of claim 9 wherein the reaction vessel is capable of temperature ranges from −150° C. to 350° C.

13. The chemical process of claim 9 wherein the micro flow reactor is configured to alter and regulate the rate of reaction fluid flow and the residence times within the pre-fabricated channels.

14. The chemical process of claim 13 wherein the rate of reaction fluid flow is within the range of 0.000100 mL/minute-500 L/min.

15. The chemical process of claim 13 wherein the residence times are within the range of 1.0 seconds-100 h.

16. A chemical process that uses a solvent blend, an amine solvent blend, an oxidant, an indene, and a metal salt to form 1,2,3,4-tetrahydroisoquinolines using a reaction vessel comprising the steps of:
Combining the indene and the solvent blend for a specified period of time;
Adding the metal salt followed by the oxidant;

Removing the solvent and adding the amine solvent blend; and

Cooling and adding a reducing agent.

17. The chemical process of claim 16 wherein the solvent blend-comprises water that contains an organic solvent.

18. The chemical process of claim 16 wherein the organic solvent comprises one of tetrahydrofuran and a methanol comprising amine.

19. The chemical process of claim 16 wherein the amine solvent blend-comprises methanol and an acid and an amine.

20. The chemical process of claim 19 wherein the amine comprises a substituted primary amine.

21. The chemical process of claim 16 wherein the oxidant comprises a periodate oxidant.

22. The chemical process of claim 16 wherein the 1,2,3,4-tetrahydroisoquinolines are obtained in 0.5 hours.

23. The chemical process of claim 16 wherein the 1,2,3,4-tetrahydroisoquinolines are obtained in 12 hours.

24. The chemical process of claim 19 wherein the amine solvent blend-contains two solvent mixtures wherein:

Solvent 1 contains the methanol and the acid; and

Solvent 2 contains the methanol and the amine.

* * * * *